(12) United States Patent
Frey et al.

(10) Patent No.: US 6,922,081 B2
(45) Date of Patent: Jul. 26, 2005

(54) ELECTRONIC CIRCUIT, SENSOR ARRANGEMENT AND METHOD FOR PROCESSING A SENSOR SIGNAL

(75) Inventors: Alexander Frey, Taufkirchen (DE); Christian Paulus, Weilheim (DE); Roland Thewes, Gröbenzell (DE)

(73) Assignee: Infineon Technologies AG (DE)

( * ) Notice: Subject to any disclaimer, the term of this patent is extended or adjusted under 35 U.S.C. 154(b) by 57 days.

(21) Appl. No.: 10/399,355

(22) PCT Filed: Oct. 16, 2001

(86) PCT No.: PCT/DE01/03949

§ 371 (c)(1),
(2), (4) Date: Sep. 8, 2003

(87) PCT Pub. No.: WO02/33397

PCT Pub. Date: Apr. 25, 2002

(65) Prior Publication Data

US 2004/0041717 A1  Mar. 4, 2004

(30) Foreign Application Priority Data

Oct. 16, 2000   (DE) ........................................ 100 51 178

(51) Int. Cl.[7] ..................... H03K 19/0175; G01R 27/26
(52) U.S. Cl. ......................... 326/88; 327/205; 327/206; 324/663; 324/117 R; 204/403.14; 435/6
(58) Field of Search ............................. 326/88; 327/205, 327/206, 72–75, 77–82; 435/6, 287.2; 324/663, 117 R, 76.77; 204/403.14

(56) References Cited

U.S. PATENT DOCUMENTS

| 4,306,196 A | 12/1981 | Dwarakanath et al. |
| 4,322,687 A | 3/1982 | Dwarakanath et al. |
| 4,462,002 A | 7/1984 | Schade, Jr. |
| 4,495,470 A | 1/1985 | Bristol |
| 4,725,348 A * | 2/1988 | Diekmann ................... 204/613 |
| 4,810,973 A | 3/1989 | Kurz |
| 4,987,379 A | 1/1991 | Hughes |
| 4,992,755 A | 2/1991 | Seevinck et al. |
| 5,233,543 A * | 8/1993 | Hoglund et al. ............ 702/126 |
| 5,726,597 A | 3/1998 | Petty et al. |
| 5,793,230 A * | 8/1998 | Chu et al. ...................... 327/77 |
| 5,880,614 A * | 3/1999 | Zinke et al. ................. 327/205 |
| 6,002,355 A | 12/1999 | Del Signore et al. |
| 6,445,171 B2 * | 9/2002 | Sandquist et al. ...... 324/117 R |

FOREIGN PATENT DOCUMENTS

| DE | 19609621 C1 | 7/1997 |
| DE | 19610115 A1 | 9/1997 |
| EP | 0939483 | 9/1999 |
| GB | 2099247 | 12/1982 |
| WO | WO93/22678 | 11/1993 |
| WO | WO/01/75149 | 10/2001 |

OTHER PUBLICATIONS

K. Hoffman, VLSI—Entwurf, Oldenburg Verlag Müanchen, Vienna, ISBN 3–486–23870–1, Seite 308, 1996.

(Continued)

*Primary Examiner*—Vibol Tan
(74) *Attorney, Agent, or Firm*—Jeffrey R. Stone; Altera Law Group, LLC

(57) ABSTRACT

In a first phase a first sensor signal, essentially comprising the current offset signal of the sensor, is applied to the input of an electronic circuit. The first sensor signal is fed to a first signal path and stored therein. In a second phase a second sensor signal, comprising the current offset signal and a time-dependent measured signal, is applied to the input and the stored first sensor signal is fed to the input by means of the first signal path, such that essentially the time dependent measured signal is fed by means of a second signal path coupled to the input.

16 Claims, 11 Drawing Sheets

OTHER PUBLICATIONS

Elektor, Nov. 1998, Applikator, MLX90308, Programmierbares Sensor–Interface, (programmable sensor interface), pp. 72–75.

"Microbiosensors using electrodes made in Si–technology", R. Hintsche, et al., 1997 Birknauser Vertag Basel/Switzerland, pp. 267–283.

"Voltammetric Multichannel Measurements Using Silicon Fabricated Microelectrode Arrays", Paeschke, et al., Received Nov. 3, 1995, Final Version Jan. 5, 1996, 8 pgs.

"Nanoscaled Interdigitated Electrode Arrays for Biochemical Sensors", Van Gerwen, et al., 1997 International Conference on Solid–State Sensors and Actuators, Chicago, Jun. 16–19, 1997, pp. 907–910.

"Capacitive Detection of Surfactant Adsorption on hydrophobized Gold Electrodes", Krause, et al., Institute of Analytical Chemistry, Chemical Sensors and Biosensors, University of Regensburg, 93040 Regensburg. Germany, Received Feb. 29, 1996, pp. 6059–6064.

"Capacitive monitoring of protein immobilization and antigen–antibody reactions on monomolecular alkylthiol films on gold electrode", Mirsky, et al., Biosensors & Bioelectronics vol. 12., No. 9–10 pp. 977–089, 1997.

"Universal sensor interface chip (USIC): specification and applications outline", P.D. Wilson, et al., Sensor Review, vol. 16, No. 1, 1996, pp. 18–21.

* cited by examiner

PRIOR ART

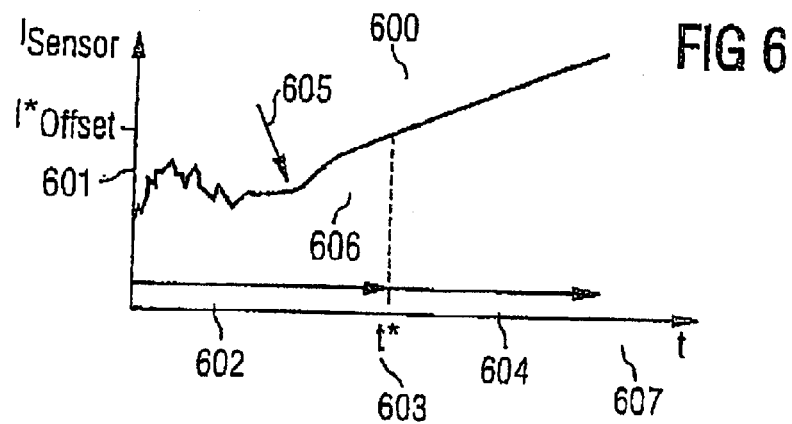
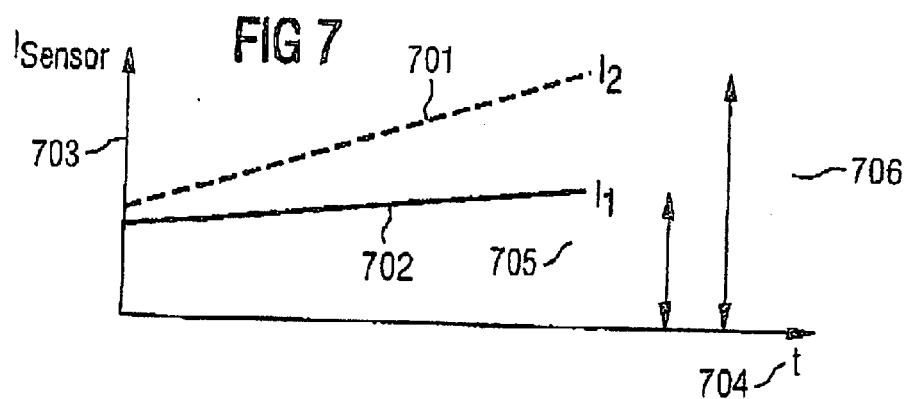
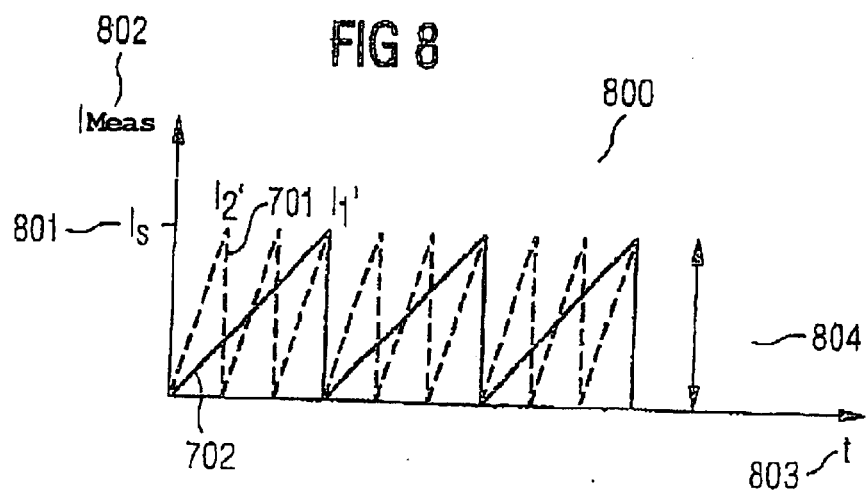

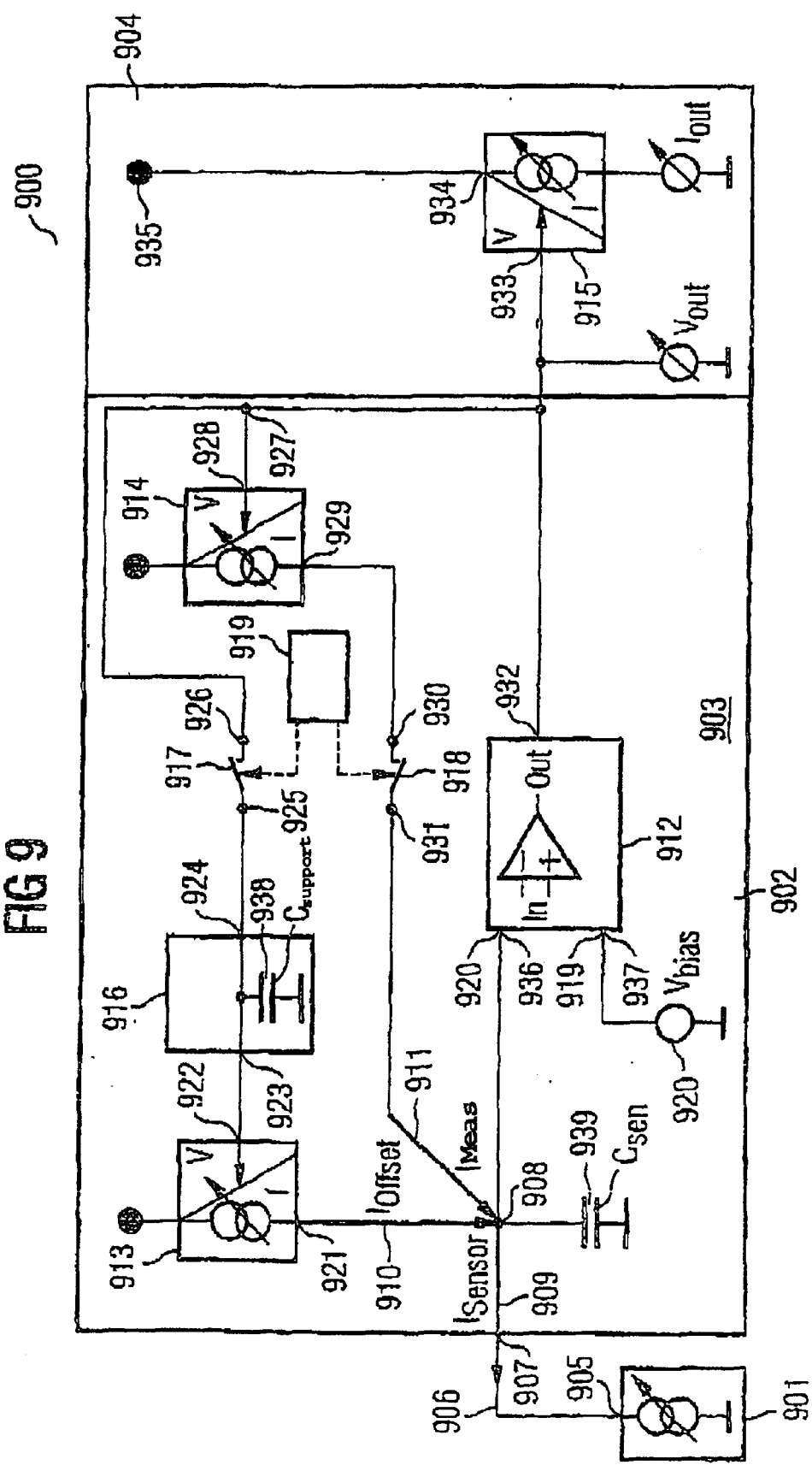

ELECTRONIC CIRCUIT, SENSOR ARRANGEMENT AND METHOD FOR PROCESSING A SENSOR SIGNAL

BACKGROUND OF THE INVENTION

1. Field of the Invention

The invention relates to an electronic circuit, a sensor arrangement and a method for processing a sensor signal.

2. Description of the Related Prior Art

Such a sensor arrangement is known as a biosensor chip from R. Hintsche et al., Microbiosensors Using Electrodes Made in Si-Technology, Frontiers in Biosensorics, Fundamental Aspects, edited by F. W. Scheller et al., Dirk Hauser Verlag. Basel, pp. 267–283, 1997.

FIG. 2a and FIG. 2b show such a biosensor chip, as described in R. Hintsche et al., Microbiosensors Using Electrodes Made in Si-Technology, Frontiers in Biosensorics, Fundamental Aspects, edited by F. W. Scheller et al., Dirk Hauser Verlag. Basel, pp. 267–283, 1997. The sensor 200 has two electrodes 201, 202 made of gold, which are embedded in an insulating layer 203 of insulating material. Connected to the electrodes 201, 202 are electrode terminals 204, 205, to which the electronic potential applied to the electrodes 201, 202 can be supplied. The electrodes 201, 202 are arranged as planar electrodes. DNA probe molecules 206 are immobilized on each electrode 201, 202 (cf. FIG. 2a). The immobilization is carried out in accordance with the gold-sulfur coupling. The analyte to be investigated, for example an electrolyte 207, is applied to the electrodes 201, 202.

If DNA strands 208 with a sequence which is complementary to the sequence of the DNA probe molecules 206 are contained in the electrolyte 207, then these DNA strands 208 hybridize with the DNA probe molecules 206 (cf. FIG. 2b).

Hybridization between a DNA probe molecule 206 and a DNA strand 208 takes place only when the sequences of the respective DNA probe molecule 206 and of the corresponding DNA strand 208 are complementary to each other. If this is not the case, then no hybridization takes place. Thus, a DNA probe molecule with a predefined sequence is in each case only capable of bonding a specific DNA strand, specifically that one with a respectively complementary sequence, that is to say of hybridizing with it.

If hybridization takes place, then as can be seen from FIG. 2b, the value of the impedance between the electrodes 201 and 202 changes. This changed impedance is determined by applying an alternating voltage with an amplitude of approximately 50 mV to the electrode terminals 204, 205 and the current resulting from this by means of a connected measuring instrument (not illustrated).

In the event of hybridization, the capacitive component of the impedance between the electrodes 201, 202 is reduced. This can be attributed to the fact that both the DNA probe molecules 206 and the DNA strands 208, which possibly hybridize with the DNA probe molecules 206, are nonconductive and thus, as can be seen, shield the respective electrode 201, 202 electronically to a certain extent.

In order to improve the measurement accuracy, it is known from P. van Gerwen, Nanoscaled Interdigitated Electrode Arrays for Biochemical Sensors, IEEE, International Conference on Solid-State Sensors and Actuators, Chicago, pp. 907–910, 16.–19. Jun. 1997 to use a large number of electrode pairs 201, 202 and to connect these in parallel, these being arranged intermeshed with one another, as can be seen, so that the result is what is known as an interdigital electrode 300 (cf. FIG. 3). The dimension of the electrodes and the distances between the electrodes are of the order of magnitude of the length of the molecules to be detected, that is to say of the DNA strands 208, or below that, for example in the region of 200 nm and below.

Furthermore, principles relating to a reduction/oxidation recycling procedure for detecting macromolecular biopolymers are known from M. Paeschke et al., Voltammetric Multichannel Measurements Using Silicon Fabricated Microelectrode Arrays, Electroanalysis, Vol. 7, No. 1, pp. 1–8, 1996 and R. Hintsche et al., Microbiosensors using electrodes made in Si-technology, Frontiers in Biosensorics, Fundamental Aspects, edited by F. W. Scheller et al., Birkhauser Verlag, Basel, Switzerland, 1997. The reduction/oxidation recycling procedure, also designated the redox recycling procedure below, will be explained in more detail below using FIG. 4a to FIG. 4c.

FIG. 4a shows a biosensor chip 400 having a first electrode 401 and a second electrode 402, which are applied to a substrate 103 as insulating layer.

A holding region, designed as a holding layer 404, is applied to the first gold electrode 401. The holding region serves to immobilize DNA probe molecules 405 on the first electrode 401.

No such holding region is provided on the second electrode.

If, by means of the biosensor 400, DNA strands with a sequence which is complementary to the sequence of the immobilized DNA probe molecules 405 are to be detected, then the sensor 400 is brought into contact with a solution 406 to be investigated, for example an electrolyte, in such a way that DNA strands possibly contained in the solution 406 to be investigated can hybridize with the complementary sequence to the sequence of the DNA probe molecules 405.

FIG. 4b shows the case in which the DNA strands 407 to be registered are contained in the solution 406 to be investigated and have hybridized with the DNA probe molecules 405.

The DNA strands 407 in the solution to be investigated are marked with an enzyme 408, with which it is possible to cleave molecules described below into part molecules.

It is usual to provide a considerably larger number of DNA probe molecules 405 than there are DNA strands 407 to be determined in the solution 406 to be investigated.

After the DNA strands possibly contained in the solution 406 to be investigated and having the enzyme 408 have hybridized with the immobilized DNA probe molecules 407, the biosensor chip 400 is rinsed, by which means the unhybridized DNA strands are removed and the biosensor chip 400 is cleaned of the solution 406 to be investigated.

This rinsing solution used for rinsing or a further solution supplied on its own in a further phase has an electronically uncharged substance added to it, which contains molecules which can be cleaved by the enzyme on the hybridized DNA strands 407, into a first part molecule 410 having a negative electronic charge and into a second part molecule having a positive electronic charge.

As FIG. 4c shows, the negatively charged first part molecules 410 are attracted to the positively charged anode, that is to say to the first electrode 401, as indicated by the arrow 411 in FIG. 4c.

The negatively charged first part molecules 410 are oxidized at the first electrode 401, which has a positive electronic potential as anode, and are attracted as oxidized part molecules 413 to the negatively charged cathode, that is to say the second electrode 402, where they are reduced again. The reduced part molecules 414 again migrate to the first electrode 401, that is to say to the anode.

In this way, a circular electronic current is generated, which is proportional to the number of charge carriers respectively generated by the enzymes 408.

The electronic parameter which is evaluated in this method is the change in the electronic current $$m = \frac{dI}{dt}$$

as a function of the time t, as illustrated schematically in the graph 500 in FIG. 5.

FIG. 5 shows the function of the electronic current 501 as a function of the time 502. The curve 503 which results exhibits an offset current $I_{offset}$ 504, which is independent of the time curve.

The offset current $I_{offset}$ 504 is generated by parasitic components on account of non-ideal states of the biosensor 400.

A substantial cause of the offset current $I_{offset}$ 504 resides in the fact that the covering of the first electrode 401 with DNA probe molecules 405 is not carried out in an ideal manner, that is to say not completely densely.

In the event of completely dense coverage of the first electrode 401 with DNA probe molecules 405, the result would be only purely capacitive electronic coupling between the first electrode 401 and the electronically conductive solution 406 to be investigated, because of what is known as the double-layer capacitance which is produced by the immobilized DNA probe molecules 405.

However, the incomplete coverage leads to parasitic current paths between the first electrode 401 and the solution 406 to be investigated, which inter alia also have non-reactive components.

However, in order to permit the oxidation/reduction process, the coverage of the first electrode 401 with the DNA probe molecules 405 may not be complete, in order that the electronically charged part molecules, that is to say the negatively charged first part molecules, are attracted to the first electrode 401 at all.

On the other hand, in order to achieve the greatest possible sensitivity of such a biosensor, in conjunction with low parasitic effects, the coverage of the first electrode 401 with DNA probe molecules 405 should be as dense as possible.

In order to achieve high reproducibility of the measured values determined by such a biosensor 400, both electrodes 401, 402 must always provide an adequately large area for the oxidation/reduction process in the context of the redox recycling procedure.

In the case of the biosensor according to the prior art, the result is thus a certain measurement uncertainty when determining the DNA strands in a solution to be investigated.

Macromolecular biopolymers are to be understood in the following text as, for example, proteins or peptides or else DNA strands with a respectively predefined sequence.

If proteins or peptides are to be registered as macromolecular biopolymers, then the first molecules and the second molecules are ligands, for example active substances with a possible binding activity, which bind the proteins or peptides to be registered to the respective electrode on which the appropriate ligands are arranged.

Possible ligands are enzyme agonists or enzyme antagonists, pharmaceuticals, sugars or antibodies or any kind of molecule which has the capability of bonding proteins or peptides specifically.

If the macromolecular biopolymers used are DNA strands with a predefined sequence, which are to be registered by means of the biosensor, then by means of the biosensor, DNA strands with a predefined sequence can be hybridized with DNA probe molecules with the sequence complementary to the sequence of the DNA strands as molecules on the first electrode.

Within the context of this description, a probe molecule is to be understood both as a ligand and as a DNA probe molecule.

The value m is proportional to the electrode area of the electrodes used to register the measurement current. Given a constant width of the electrodes, the value m is thus proportional to the longitudinal extent of the electrodes used, for example in the case of the first electrode 201 and the second electrode 202, to their length perpendicular to the plane of the drawing in FIG. 2a and FIG. 2b.

If a plurality of electrodes are connected in parallel, for example in the known interdigital electrode arrangement, then the change in the measurement current m is also proportional to the number of respectively parallel-connected electrodes.

However, the value of the change in the measurement current m can have a very highly fluctuating value range, because of different influences, in particular for different solutions to be investigated.

The cause of the high fluctuations can firstly be the dynamic range required for DNA strands with a predefined sequence to be detected, in order to permit their registration at all.

Secondly, however, it is also possible that different macromolecular biopolymers of different types to be detected will lead to highly different value ranges for the measurement signal which results, that is to say in particular the measurement current and its change m over time, which in turn leads to a widening of the required overall dynamic range for a predefined electrode configuration with subsequent uniform measuring electronics, that is to say with subsequent uniform measuring circuit.

The measurement electronics, which register the time change between the electrodes, that is to say between anode and cathode, and process it further, must function reliably and accurately in the required value ranges.

The requirements on the large dynamic range of such a circuit lead to the measurement electronics being expensive and complicated, in order to provide the required dynamic range.

In other methods also, as are known for example from P. van Gerwen, Nanoscaled Interdigitated Electrode Arrays for Biochemical Sensors, IEEE, International Conference on Solid-State Sensors and Actuators, Chicago, pp. 907–910, 16.–19. Jun. 1997, WO 93/22678, DE 196 10 115 A1, C. Krause et al., Capacitive Detection of Surfactant Adsorption on Hydrophobized Gold Electrodes, Langmuir, Vol. 12, No. 25, pp. 6059–6064, 1996, V. Mirsky et al., Capacitive Monitoring of Protein Immobilization and Antigen-Antibody Reactions on Monomolecular Alkylthiol Films on Gold Electrodes, Biosensors & Bioelectronics, Vol. 12, No. 9–10, pp. 977–989, 1997, the case can occur in which the electronic measurement signals to be detected have to be measurable over a large dynamic range.

There, too, extreme requirements on the measurement electronics, that is to say the evaluation circuit, can result with respect to their dynamics. In particular during circuit design, the non-ideal states of the components used, that is to say noise, the variation in the parameters of the components, are taken into account in the form that, for these components, a working point in the circuit design is chosen at which these non-ideal states have the lowest possible influence on the quality of the measured result. If a circuit is to be operated over a large dynamic range, maintaining an optimum working point for all the ranges becomes increasingly more difficult and more complex.

Furthermore, in particular in the requirements illustrated above, the offset current $I_{offset}$ is very much greater than the time change of the measurement current m over the entire measurement period, that is to say measuring time is $t_{meas}$, which means that the following is true $$I_{offset} >> m \cdot t_{meas}. \quad (1)$$

It is therefore necessary, within a large signal (offset current $I_{offset}$) to measure a very small time-dependent change (time change in the measurement current) with high accuracy.

The result is therefore very high requirements on the measuring instruments used.

The value of the parameter m=dI/dt can lie in a large value range for different analytes to be investigated, as presented above.

The cause for this can, firstly, be the dynamic range required for a species to be detected, but secondly it is also possible that different species to be detected lead from the start to very different value ranges for the resultant measurement signal, which in turn corresponds to a widening of the required overall dynamic range.

An electronic circuit which registers the time change of the circular current between anode and cathode and processes it further must therefore function reliably in the appropriate value range.

The requirements on the dynamic range of this circuit are therefore extremely high.

During circuit design, it is known to take into account the non-ideal states of the components used (noise, parameter variations) in the manner in which, for these components, a working point in the circuit is selected in which these non-ideal states play the smallest possible part.

If a circuit is to be operated over a large dynamic range, maintaining an optimum working point over all the ranges becomes increasingly more difficult, more complex and therefore more expensive, however.

Furthermore, the documents DE 196 09 621 C1, U.S. Pat. Nos. 5,726,597, U.S. Pat. No. 4,992,755, 4,987,379, 4,810, 973, 4,495,470, 4,462,002, 4,322,687, 4,306,196, Elektor, 11/98, Applikator, MLX90308, Programmierbares Sensor-Interface, [programmable sensor interface], pp. 72–75, 1998, P. D. Wilson et al., Universal sensor interface chip (USIC): specification and applications outline, Sensor Review, Vol. 16, No. 1, pp. 18–21, ISSN 0260-2288, 1996 disclose electric circuits for voltage offset compensation of a voltage signal on an input of an operational amplifier.

BRIEF SUMMARY OF THE INVENTION

The invention is based on the problem of determining, from a sensor signal which has a current offset signal component and a time-dependent measurement signal component, that is to say one which varies over time, the measurement signal component with improved accuracy.

The problem is solved by the electronic circuit, the sensor arrangement and the method for processing a sensor signal having the features as claimed in the independent patent claims.

An electronic circuit for processing a first sensor signal, which comprises a current offset signal and a time-dependent measurement signal, or a second sensor signal which substantially comprises the current offset signal, has an input to which the first sensor signal or the second sensor signal can be applied. The input is coupled to a first signal path for leading the current offset signal away and also to a second signal path for leading the time-dependent measurement signal away.

A control unit is also provided. The control unit is set up such that, in the electronic circuit, control is carried out in a way in which, for the case in which the second sensor signal is applied to the input of the electronic circuit, the second sensor signal is carried substantially only by the first signal path.

Clearly this means that, by means of the control carried out by the control unit, a signal component which is still carried by the second signal path at the start of the control is substantially completely carried by the first signal path after the control has been completed. Thus, in other words, with the aid of a suitable electronic circuit, the control unit, the first sensor signal is registered and complete outward flow into the offset channel provided for this purpose, that is to say the first signal path, is forced.

Since the first sensor signal substantially comprises only the current offset component of the sensor signal, that is to say for example the offset current, the control unit ensures that the entire offset current is carried in the first signal path which, in the case of an offset current, represents a first current path.

The first sensor signal is generated, for example, by the sensor supplying a sensor signal although no molecules to be registered are yet being led to the sensor. As can be seen, the first sensor signal thus represents the sensor in the state, for example, uncovered by macromolecular biopolymers to be registered.

The first signal path contains a voltage value storage element, with which the second sensor signal can be stored when the second sensor signal is applied to the input. The voltage value storage element, as can be seen, is thus used to store substantially the current offset component of the sensor signal.

If the first sensor signal is applied to the input, the second sensor signal stored in the voltage value storage element is supplied to the input.

Since in this case both the second sensor signal with the current offset signal and the time-dependent measurement signal, and also the first sensor signal and therefore substantially the current offset signal are supplied to the input, and the second signal path is also coupled to the input, that is to say the input junction, as can be seen, the result according to Kirchhoff's law is that substantially only the time-dependent measurement signal flows into the second signal path.

In this way, very simple and nevertheless very accurate current offset compensation of the current offset component of the sensor signal is achieved.

The electric circuit is therefore suitable in particular for use when registering macromolecular biopolymers in whose context the current offset component of the sensor signal can be several orders of magnitude greater than the measurement signal component.

The electric circuit is therefore suitable in particular for use in a sensor arrangement, preferably in a biosensor arrangement, for example in a biosensor chip, in which both the sensor as sensor signal generator and the electronic circuit as evaluation circuit are integrated.

In a method for processing a sensor signal which comprises a current offset signal and a time-dependent measurement signal, in a first phase, a first sensor signal is applied to an input of an electronic circuit, the first sensor signal substantially comprising the current offset signal. The first sensor signal is substantially led into a first signal path coupled to the input and stored there, preferably in a signal storage element.

In a second phase, a second sensor signal is applied to the input, the second sensor signal comprising the current offset signal and a time-dependent measurement signal. In the second phase, the stored first sensor signal is supplied to the input via the first signal path, so that the time-dependent measurement signal is substantially carried by a second signal path coupled to the input.

As explained above, both the electronic circuit and the method are suitable in particular for use when detecting macromolecular biopolymers.

In particular, the sensor arrangement is suitable for use in the redox recycling process described above. In this case, the redox recycling process is carried out during the second phase, and the current profile determined is supplied as a second sensor signal to the electronic circuit, in which the measurement signal component, that is to say the measurement current, is separated from the offset current.

Macromolecular biopolymers are to be understood, for example, as proteins or peptides or else DNA strands with a respectively predefined sequence.

If proteins or peptides are to be detected as the macromolecular biopolymers, then the molecules are ligands, for example active substances with a possible binding activity, which bind the proteins or peptides to be detected to the respective electrode on which the appropriate ligands are arranged.

Possible ligands are enzyme agonists or enzyme antagonists, pharmaceuticals, sugar or antibodies or any kind of molecule which has the capability of binding proteins or peptides specifically.

If the macromolecular biopolymers used are DNA strands with a predefined sequence, which are to be detected by means of the biosensor, then by means of the biosensor DNA strands with a predefined sequence can be hybridized with DNA probe molecules with the sequence complementary to the sequence of the DNA strands as molecules on the first electrode of a sensor described above in connection with the prior art.

Within the context of this description, a probe molecule is to be understood both as a ligand and as a DNA probe molecule.

The holding region of the first electrode can be coated with a material which can immobilize probe molecules.

The holding region of the first electrode can also be equipped to hold ligands, with which peptides or proteins can be bound.

The holding region of the first electrode can also be equipped to hold DNA probe molecules, with which DNA molecules can be bound.

The first holding region can contain at least one of the following materials:

Hydroxyl radicals,
Epoxy radicals,
Amine radicals,
Acetoxy radicals,
Isocyanate radicals,
Succinimidyl ester radicals,
Thiol radicals,
Gold,
Silver,
Platinum,
Titanium.

The enzyme used can be, for example a-galactosidase,
b-galactosidase,
b-glucosidase,
a-mannosidase,
Alkaline phosphatase,
Acidic phosphatase,
Oligosaccharide dehydrogenase,
Glucose dehydrogenase,
Laccase,
Tyrosinase,
or enzymes of the related type.

It should be noted that low molecular weight enzymes have the highest reaction efficiency and can therefore also ensure the highest sensitivity.

The further solution therefore contains molecules which can be cleaved by the enzyme into a first part molecule with a negative electronic charge and into a second part molecule with a positive electronic charge.

The cleavable molecule that can be used within the context of the redox recycling process is primarily, for example p-aminophenyl hexopyranoside,
p-aminophenyl phosphate,
p-nitrophenyl hexopyranoside,
p-nitrophenyl phosphate, or
suitable derivatives of
  a) diamines,
  b) catecholamines,
  c) $Fe(CN)_6^{4-}$,
  d) Ferrocene,
  e) Dicarboxylic acid,
  f) Ferrocene lysine,
  g) Osmium bipyridyl-NH, or
  h) PEG ferrocene2.

According to one refinement of the invention, the electronic circuit has an output at which an output signal can be tapped off, which substantially corresponds to the measurement signal in the second sensor signal. Furthermore, according to this refinement of the invention, a switching element is provided with which the first signal path or the second signal path can be coupled to the output independently of each other or can be separated from the output.

In this way, it becomes very simply possible to emulate, that is to say to implement, the two phases in the method in the electronic circuit.

The voltage value storage element can have at least one capacitor, with which analog storage of the first sensor signal in the storage element of the first signal path is made reliably possible in a very simple way.

Alternatively, the voltage value storage element can be configured as a digital memory, in which the digital value of the current offset signal, produced by an analog/digital converter, that is to say substantially the value of the first current signal, is stored. In the second phase, in this case the stored digital value is supplied to a digital/analog converter, and in the latter a signal substantially corresponding to the first sensor signal is generated and supplied to the input for current offset compensation.

According to a further refinement of the invention, the first signal path has a first current source controlled by the control unit, with which the offset current is provided for the current offset compensation in the second phase.

The control unit can be set up in such a way that, for the case in which the signal carried by the second signal path exceeds a predefined threshold value, the controlled first current source generates a current corresponding to the signal carried by the second signal path, which current can be supplied to the input.

In this way, the maintenance of a predefined suitable dynamic range can be ensured, since if the threshold value is exceeded, this signal occurring in the second signal path is stored as the current offset signal in the signal storage element of the first signal path and therefore, as can be seen, "resetting" of the dynamic range is achieved, which means that a fixed dynamic range for the measurement channel, that is to say the second signal path, is ensured.

The control unit can have a voltage source. In this case, the first controlled current source can be a current source which is voltage-controlled by the voltage source.

The voltage source itself can be configured as a voltage-controlled voltage source, preferably as a differential-voltage-controlled voltage source.

According to a further refinement of the invention, a controlled second current source is provided in the second signal path, and can be controlled by a further voltage source.

A controlled third current source, which generates the output signal, can be connected between the output and the signal paths.

Exemplary embodiments of the invention are illustrated in the figures and will be explained in more detail below.

BRIEF DESCRIPTION OF THE DRAWINGS

In the figures:

FIG. 6 shows a graph in which the signal curve in the two phases, the current offset compensation and the actual measuring phase, is illustrated;

FIG. 7 shows a schematic representation of different dynamic ranges for the sensor signal for two different measurement situations;

FIG. 8 shows a schematic representation of the "reset method" for achieving a uniform fixed dynamic range for the sensor signals from FIG. 7;

FIG. 9 shows a basic circuit diagram of an electronic circuit according to one exemplary embodiment of the invention;

DETAILED DESCRIPTION OF THE INVENTION

Figure 14:
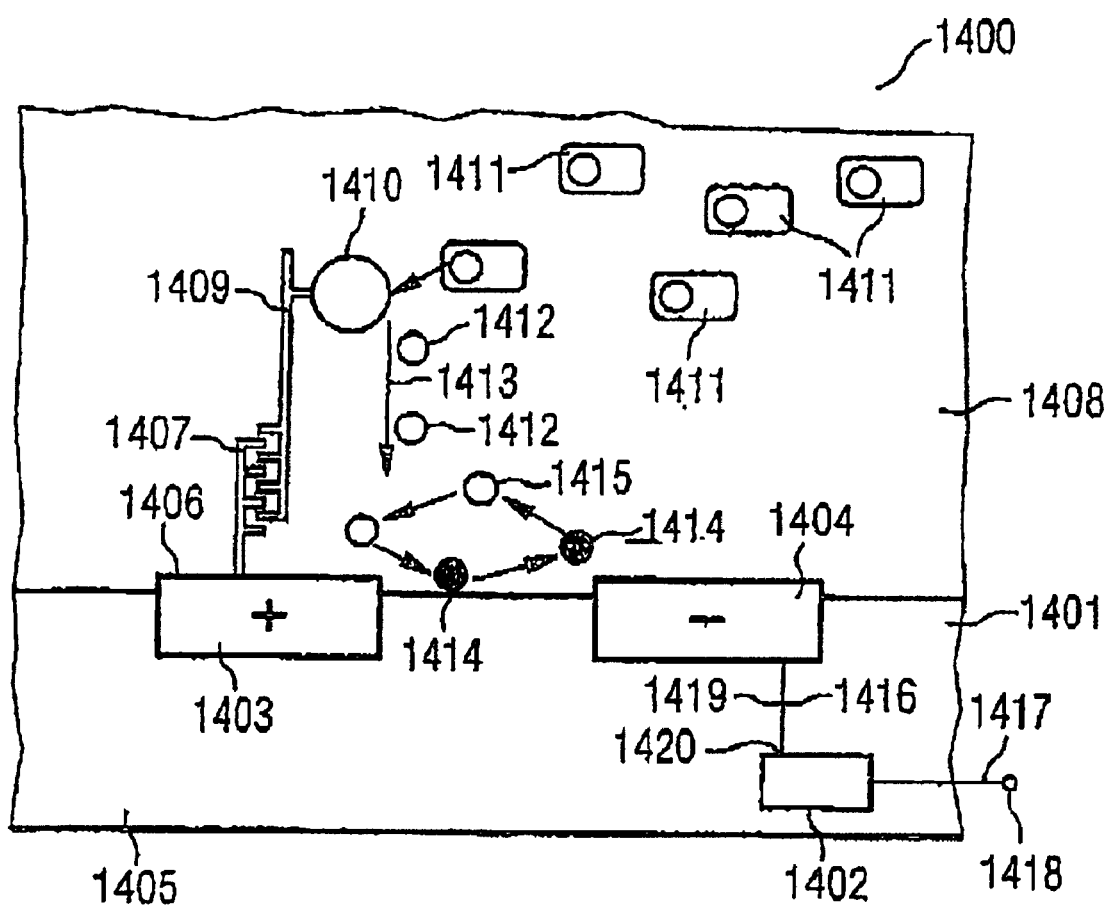
FIG. 14 shows the sketch of a sensor arrangement comprising a sensor and an electronic circuit which are implemented in an integrated circuit.

FIG. 14 shows a sensor arrangement 1400 comprising a sensor 1401 and an electronic circuit 1402, the sensor 1401 and the electric circuit 1402 being integrated in a common electric circuit in the sensor arrangement 1400.

Figure 4A:
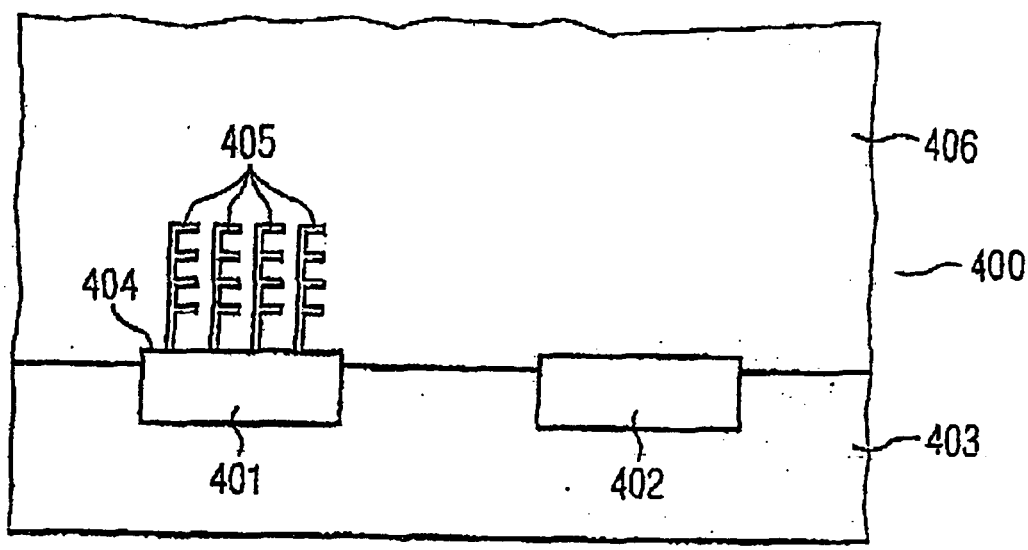
FIGS. 4a to 4c show sketches of a biosensor according to the prior art, by using which individual states within the context of the redox recycling procedure are explained.
Figure 4B:
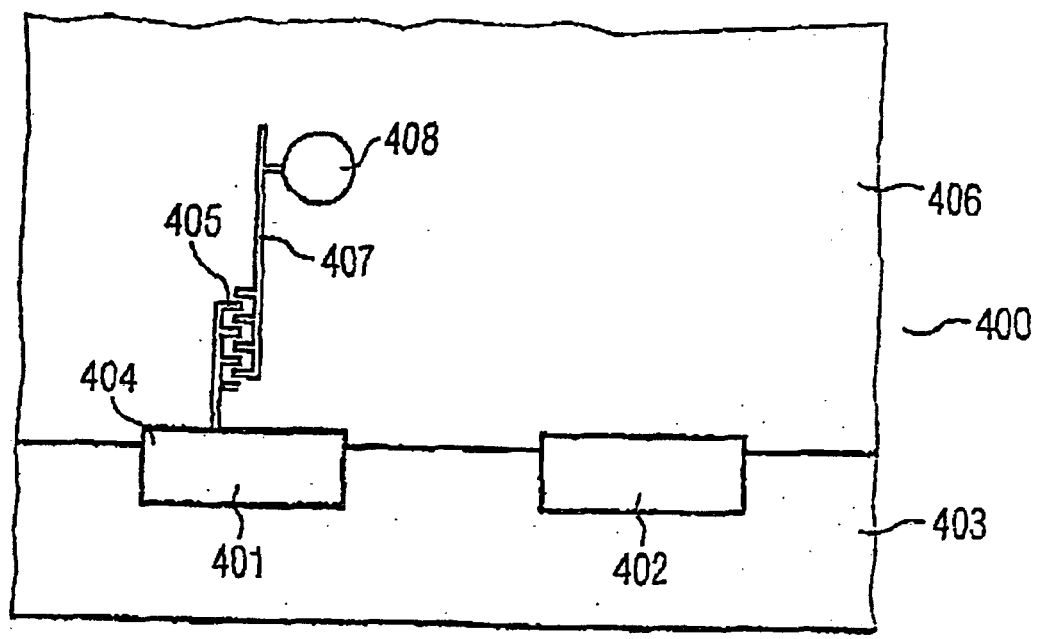
Figure 4C:
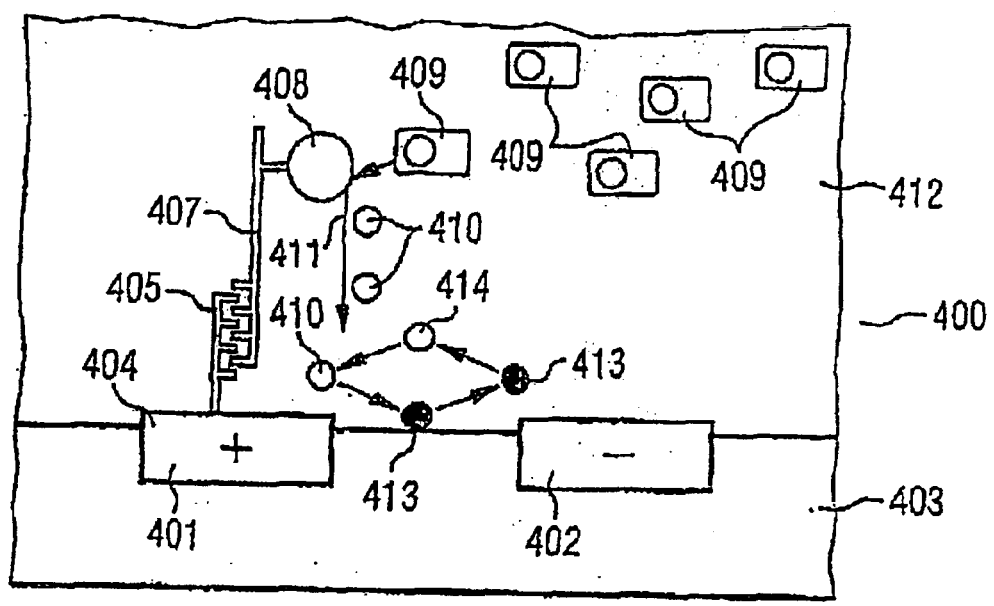

The sensor 1401 has substantially the structure of the structure illustrated in FIG. 4a to FIG. 4c.

This means that the sensor 1401 comprises a first electrode 1403 and a second electrode 1404, which are applied to a substrate 1405 as insulating layer. The electric circuit 1402 is also introduced into the substrate 1405.

Applied to the first electrode 1403 of gold is a holding region, equipped as a holding layer 1406. The holding region is used to immobilize DNA probe molecules 1407 on the first electrode 1403.

No such holding region is provided on the second electrode 1404.

FIG. 14 shows the sensor arrangement 1400 in the measuring phase, that is to say in the phase in which, by means of the sensor arrangement 1400, DNA strands with a sequence which is complementary to the sequence of the immobilized DNA probe molecules 1407 are to be detected.

For this purpose, the sensor 1401 is brought into contact with a solution 1408 to be investigated, for example an electrolyte, in such a way that DNA strands that may possibly be contained in the solution 1408 to be investigated and having the complementary sequence to the sequence of the DNA probe molecules 1407 can hybridize.

According to the case illustrated in FIG. 14, the DNA strands 1409 to be detected are contained in the solution 1408 to be investigated and are already immobilized on the DNA probe molecules 1407.

The DNA strands 1409 in the solution 1408 to be investigated are marked with an enzyme 1410, with which enzyme 1410 it is possible to cleave molecules described below into part molecules.

The enzyme 1410 used is one of the enzymes mentioned above.

It is usual to provide a considerably larger number of DNA probe molecules 1407 than DNA strands 1409 to be determined are contained in the solution 1408 to be investigated.

After the DNA strands detected possibly contained in the solution 1408 to be investigated and having the enzyme 1410 have hybridized with the immobilized DNA probe molecules 1407, the sensor 1401 which, according to this exemplary embodiment, functions as a biosensor, is rinsed, as a result of which the unhybridized DNA strands are removed and the sensor 1401 is cleaned of the solution 1408 to be investigated.

This rinsing solution used for rinsing or a further solution fed in on its own in a further phase has an electronically uncharged substance added to it which contains molecules 1411 which can be cleaved by the enzyme 1410 on the hybridized DNA strands 1409, into a first part molecule 1412 having a negative electric charge and into a second part molecule (not illustrated) with a positive electric charge.

The first part molecules 1412 which are produced from the molecules 1411 that can be cleaved by the enzyme 1410 and which have a negative electric charge are attracted to the positively charged anode, that is to say to the first electrode 1403, as shown in FIG. 14, and as symbolized by the arrow 1413.

The negatively charged first part molecules 1412 are oxidized at the first electrode 1403 which, as the anode, has a positive electric potential, and as oxidized, electrically positively charged part molecules 1414, are moved to the negatively charged cathode, that is to say the second electrode 1404, that is to say are attracted by the latter, at which second electrode 1404 they are reduced again. The reduced part molecules 1415 are in turn moved to the first electrode 1403, that is to say to the anode.

In this way, a circular electric current is generated which is proportional to the number of electric charge carriers respectively generated by the enzymes 1410.

Figure 5:
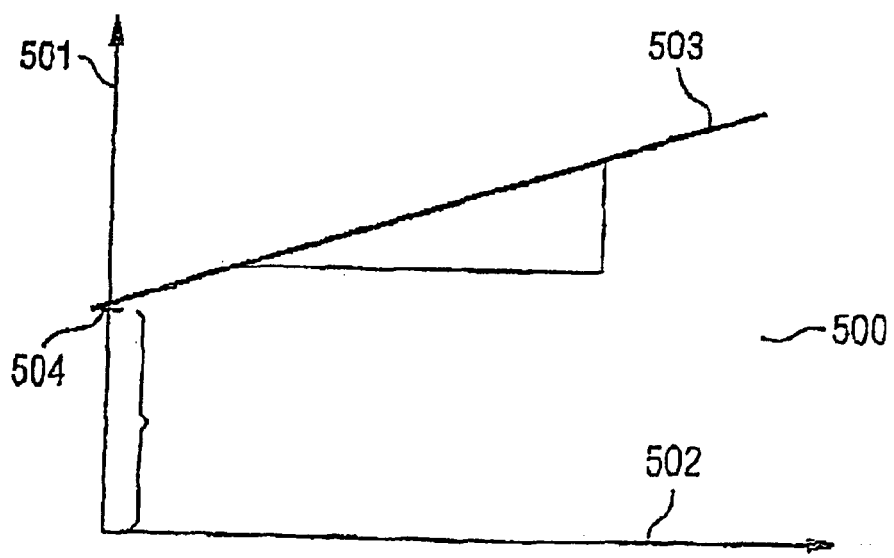
FIG. 5 shows a functional curve of a circular current within the context of a redox recycling procedure.

As has already been described above, the electronic parameter which is evaluated in this method is the change in the electric current $$m = \frac{dI}{dt}$$

as a function of the time t, as illustrated schematically in the graph 500 in FIG. 5.

The measurement current generated, as the sensor signal 1416 from the second electrode 1404, is fed to the electronic circuit 1402, as is explained in more detail below, as the second sensor signal in the actual measuring phase.

As will be explained in further detail below, the electric circuit 1402 divides the offset current from the actual measurement current, that is to say from the time-varying measurement signal, which is provided as an output signal 1417 on an output 1418 of the electronic circuit 1402.

Figure 1:
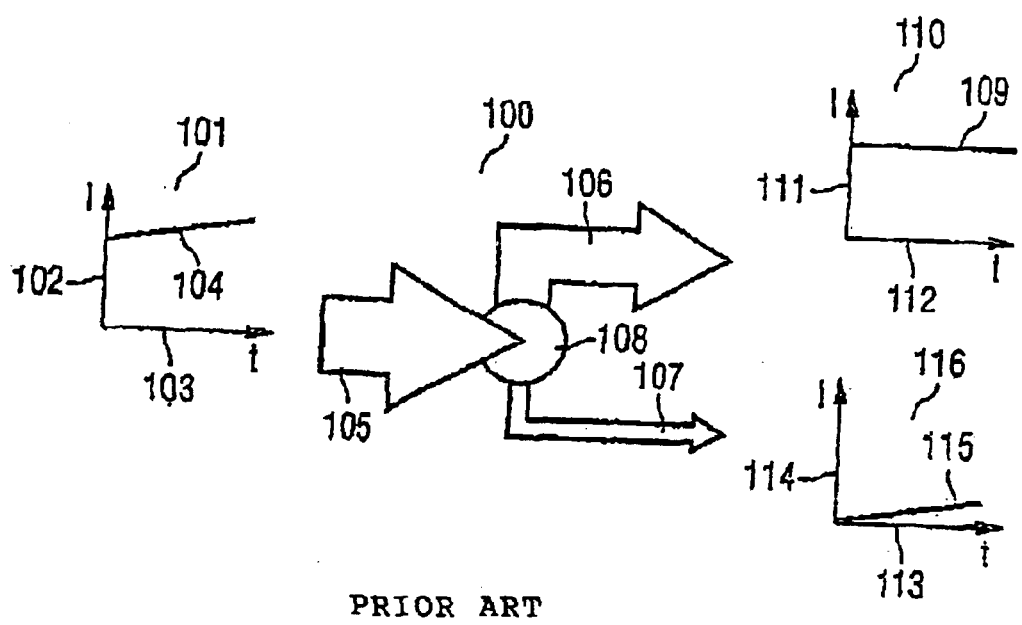
FIG. 1 shows a basic sketch, in which the principle on which the exemplary embodiments are based is illustrated.
Figure 2A:
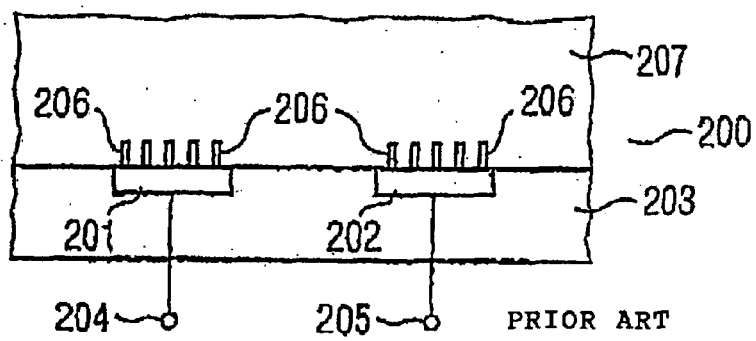
FIGS. 2a and 2b show a sketch of two planar electrodes, by means of which the existence of DNA strands to be detected in an electrolyte (FIG. 2a) or their nonexistence (FIG. 2b) can be detected.
Figure 2B:
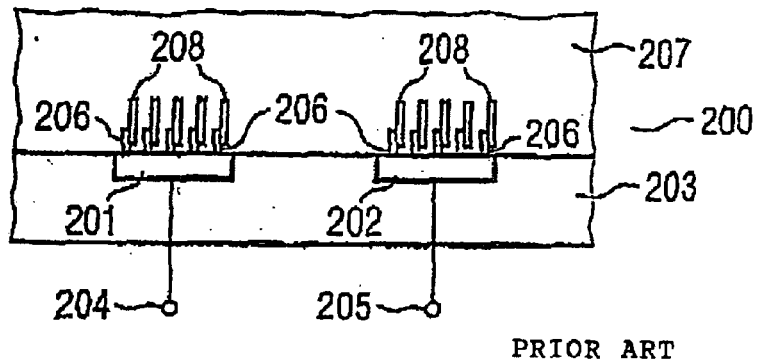
Figure 3:
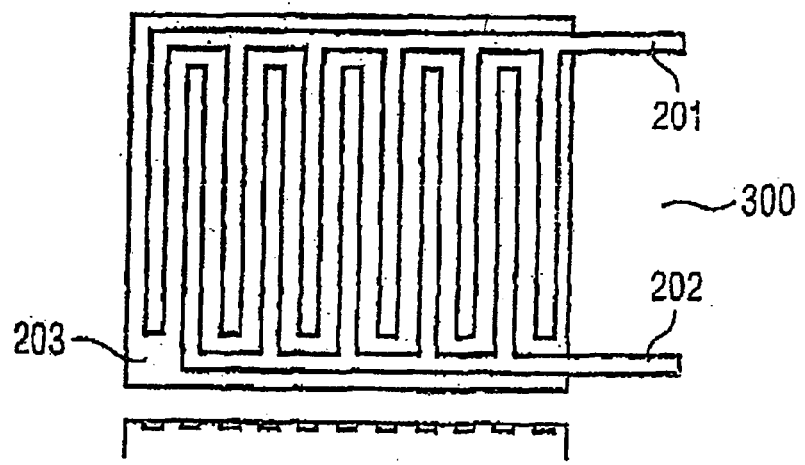
FIG. 3 shows interdigital electrodes according to the prior art.

For the purpose of further illustration, FIG. 1 shows a basic sketch 100 of the principle on which the further exemplary embodiments of the invention are based.

In the basic sketch 100 in FIG. 1, a first graph 101 is shown in which the curve of the sensor signal 1416 generated by the sensor 1402 during the redox recycling process is illustrated. The curve of the current I 102 over the time t 103 results in a characteristic sensor signal curve 104, as illustrated in the first graph 101.

This second sensor signal 104 is fed to an input 1420 of the electric circuit 1402 via a sensor channel 105, in FIG. 14 by way of example via an electric line 1419, from the second electrode 1404.

As can be seen, the principle can be seen in the fact that the sensor signal 104 which contains a current offset component and a measurement signal component and which is fed to the electronic circuit 1402 via the sensor channel 105, is divided up into a current offset component and a measurement signal component, the current offset component being supplied as an offset current via an offset channel 106 and the measurement signal component, as the actual measurement current, via a measurement channel 107, that is to say the second sensor signal 104, 1416 is divided up at a node 108.

A first part is a time-independent signal, the offset current 109, whose curve is illustrated in a second graph 110 in FIG. 1 as the curve of the current I 111 as a function of the time t 112. In the following text, a time-independent signal is to be understood as a signal which does not vary over time or whose signal value is determined at a predefined time, and the signal value determined is used for a predefined time period as a constant signal value.

Via the measurement channel 107, the time-dependent component of the second sensor signal 1416 is supplied as a second part, that is to say the measurement current which is carried via the measurement channel 107 is a time-varying current curve, in the area of the redox recycling process a current I 114 which varies linearly over the time t 113, as illustrated as the measurement current curve 115 in a third graph 116 in FIG. 1.

Thus, as can be seen, a first signal path is used as a current path for carrying the offset current away, while in a second signal path, that is to say in a second current path, the remaining differential signal is derived and processed further as the measurement current.

According to the exemplary embodiments of the invention, the entire measuring process is divided up into two phases, as illustrated in FIG. 6 in a timing graph 600.

The timing graph 600 shows the curve of a sensor current $I_{sensor}$ 601 over the time t 607, which is given as the sum of the offset current $I_{offset}$ and the measurement current $I_{meas}$, the offset current $I_{offset}$ being substantially time-independent and the measurement current $I_{meas}$ being time-dependent.

In a first phase 602, current offset compensation of the offset current $I_{offset}$ is carried out.

The first phase 602 lasts from a first time t=0 to a changeover time t* 603, at which the actual measurement phase 604 for determining the time-dependent curve of the measurement current 115 begins.

In the first phase 602, the sensor 1401 generates an electric current whose time curve does not yet contain any information that can be evaluated about the macromolecular biopolymer to be detected in each case, for example the DNA strand to be detected.

This means that in the first phase 602, no redox recycling process has yet been started or only a transient process of the redox recycling process is being carried out.

With the aid of the electronic circuit 1402 explained in detail below, the electric current generated by the sensor 1401 is registered as a first sensor signal and, in the manner explained in detail below, substantially complete dissipation of the first sensor signal into the offset channel 106 provided for the purpose is "forced" by means of a suitable control system.

The first sensor signal has substantially only the current offset component, that is to say the offset current $I_{offset}$, which is generated by the sensor 1401.

After current offset compensation has been carried out in the first phase 602, the redox recycling process described above is started, symbolized in FIG. 6 by an arrow 605.

After the start of the redox recycling process, the electric current rising linearly over the time t 607 is established after a start-up phase 606.

At this time, the state of the offset channel 106 is "frozen", that is to say the value of the offset current $I_{offset}$ is stored in a suitable way in the electronic circuit 1402, as will be explained in detail below.

In the second phase 604, the actual measurement phase, in which a registration of macromolecular biopolymers takes place, each additional current contribution generated after the end of the current offset compensation, that is to say the first phase 602, by the redox recycling process is led into the measurement channel 107 and can be processed further there without the normally considerably disruptive current offset component, that is to say without the offset current $I_{offset}$.

A considerable advantage in the on-chip solution illustrated in accordance with this exemplary embodiment, in which both the sensor 1401 and the electronic circuit 1402 are implemented integrated in a chip in the sensor arrangement 1400, is to be seen in the fact that the signal component of interest, that is to say the measurement current 115, can be filtered out directly at the sensor 1401 from the second sensor signal produced.

Amplification of this signal component, that is to say the measurement current, can therefore be carried out in the measurement channel 107 independently of the restrictions according to the prior art which would result from the very large current offset component.

According to the exemplary embodiments, with the aid of the offset channel 106, provision is made to be able to reset the measurement channel 107 repeatedly, that is to say to a predefined value, in order to reinitialize the offset channel 106 again.

As has been illustrated above, the difference in the dynamic range, illustrated in FIG. 7, of two sensor signals 701, 702, as illustrated in the graph 700, can be a problem for the desired sensor signal evaluation, that is to say during registration of the measurement current from the sensor current 703 $I_{sensor}$ as a function of the time t 704.

As has been illustrated above, in the case of different DNA sequences of the DNA strands to be registered, the result is often considerably different dynamic ranges, for example a first dynamic range 705 for the first signal $I_1$ 702, and a second dynamic range 706 for a second signal $I_2$.

According to this configuration of the invention, during the redox recycling process, if a predefined threshold value is exceeded, that is to say a predefined threshold current $I_S$ 801, as illustrated in a graph 800 in FIG. 8, provision is made in the measurement channel 107 to force the measurement current $I_{meas}$ 802 respectively flowing through the measurement channel 107 as a function of the time t 803 to flow away completely into the offset channel 106, because the threshold value $I_S$ 801 has been exceeded, and then to be stored as a new offset value for the current offset compensation as a new offset current $I_{offset}$.

In the case of this procedure, the resetting illustrated in FIG. 8 is ensured, and therefore a sawtooth curve of the respective current signal 701, 702 in the measurement channel 107 is produced.

In this way, a fixed dynamic range 804, defined by the threshold current $I_S$ 801, is predefined.

FIG. 9 shows a basic circuit of a sensor arrangement 900 according to one exemplary embodiment of the invention with further details.

FIG. 9 illustrates the sensor 901 and the electronic circuit 902.

The electronic circuit 902, according to this exemplary embodiment, is divided up into a control part 903 and an output part 904.

The sensor 901 is coupled electrically to an input 907 of the electronic circuit 902 via its output 905 and an electric line 906.

Via the electric coupling, the respective sensor signal, the first sensor signal described above or the second sensor signal, is supplied as sensor current $I_{sensor}$ to the electronic circuit 902, in particular to a first node 908.

The first node 908 is coupled to the input 907 of the electronic circuit 902, which electric connection forms the sensor channel 909, and also to the offset channel 910 and the measurement channel 911.

Illustrated in idealized form in FIG. 9 are the current flow of the sensor current $I_{sensor}$, of the offset current $I_{offset}$ and of the measurement current $I_{meas}$.

Also illustrated, as output signals, are an output current $I_{out}$ and an output voltage $V_{out}$.

The electronic circuit 902 has, in its control part 903, a differential-voltage-controlled voltage source 912, and a first voltage-controlled current source 913, a second voltage-controlled current source 914 and a third voltage-controlled current source 915.

Also provided is a voltage value memory 916.

A first switch 917 is introduced into the offset channel, that is to say into the first current path 910, and a second switch 918 is introduced into the measurement channel 911, that is to say into the second current path.

The two switches 917, 918 are activated by a control unit 919 in such a way that they can be switched on or switched off independently of each other.

Depending on the switch positions of the switches 917, 918 controlled by the control unit 919, the control part 903 can be operated in two operating modes, which will be explained in more detail below.

The differential-voltage-controlled voltage source 912 is coupled via a first input 937 to a voltage source 920 that provides a bias voltage $V_{bias}$ and also to the ground potential.

A second input 936 of the differential-voltage-controlled voltage source 912 is coupled to the first node 908 of the electronic circuit 902.

A first terminal 921 of the first controlled current source 913 is coupled to the first node 908, and a second terminal 922 of the first voltage-controlled current source 913 is coupled to the voltage value memory 916 via its first terminal 923.

A second terminal 924 of the voltage value memory 916 is coupled to a first terminal 925 of the first switch 917, and a second terminal 926 of the first switch 917 is coupled to a second node 927, which is in turn coupled to a first terminal 928 of the second voltage-controlled current source 914.

A second terminal 929 of the second voltage-controlled current source 914 is also connected to a first terminal 930 of the second switch 918, whose second terminal 931 is connected to the first node 908, which forms the measurement channel, that is to say the second current path.

Furthermore, the output 932 of the differential-voltage-controlled voltage source 912 is coupled to the second node 927 and to a first terminal 933 of the third voltage-controlled current source 915, whose second terminal 934 is coupled to the output 935 of the electronic circuit 902 in the output part 904.

In a first operating mode, the switch position of the first switch 917 is closed and the second switch 918 is open.

In this state, the electronic circuit 902 effects the compensation of the offset current $I_{offset}$, which is substantially formed by the first sensor signal, as explained above, which compensation is described in the first phase 602, that is to say in the phase of current offset compensation.

Expressed in other words, this means that the sensor current $I_{sensor}$ tapped off at the second electrode 1404 is fed completely into the offset channel 106, 910 in the first phase.

This state is implemented by a control loop which is formed by the differential-voltage-controlled voltage source 912 and the first voltage-controlled current source 913.

With the aid of the voltage value memory 916, the input voltage value corresponding to the first voltage-controlled current source 913 is stored, that is to say saved.

In FIG. 9, the voltage value memory 16 is implemented as an analog memory, symbolized by means of a capacitor 938.

In this connection, it should be pointed out that the storage of the corresponding voltage value and therefore of the offset current $I_{offset}$ can also be done digitally.

The respective specific voltage value can, for example, alternately be converted by means of an analog/digital converter, stored digitally and converted back by a digital/analog converter into an analog voltage signal or the corresponding current signal, which in turn corresponds substantially to the offset current $I_{offset}$.

In a second operating mode of the electronic circuit 902 illustrated in FIG. 9, the first switch 917 is opened and the second switch 918 closed.

In this state, the electronic circuit 902 effects splitting of the sensor current $I_{sensor}$ tapped off at the sensor 901 into the two current components of the offset current $I_{offset}$ and the measurement current $I_{meas}$.

In this connection, the value of the offset current $I_{offset}$ is determined from the voltage value stored in the voltage value memory 916 at the changeover time t* 603 (cf. FIG. 6).

In the measurement channel 107, in accordance with Kirchhoff's law, the following electric current flows:

$$I_{meas} = I_{sensor} - I_{offset}. \quad (1)$$

The measurement channel 911 is a constituent part of the control loop which is formed by the differential-voltage-controlled voltage source 912 and the second voltage-controlled current source 914.

The voltage value of the output voltage $V_{out}$ and of the measurement current $I_{meas}$ are thus linked with each other via the characteristics of the second voltage-controlled current source 914.

If the characteristics of the second voltage-controlled current source 914 and of the third voltage-controlled current source 915 are implemented substantially identically to each other, or if two identical voltage-controlled current sources 914, 915 are used, then in the output part 904 of the electronic circuit 902, the voltage value of the output voltage $V_{out}$ is converted into the output current $I_{out}$ in such a way that:

$$I_{out} = I_{meas} \quad (2)$$

The output current $I_{out}$ thus contains substantially only the useful signal from the sensor 901, that is to say the time-dependent measurement current $I_{meas}$, which describes the time-dependent behavior during the redox recycling process and thus represents the conclusion about the corresponding hybridization of the DNA strands with the DNA probe molecules 1407 on the sensor 901.

The bias voltage source 920 has in particular the following function explained in more detail below.

As soon as one of the control loops described above is closed, there is established at the first node 908 or on a capacitor at this node, symbolized by a capacitor $C_{sen}$ 939, the voltage value of the bias voltage $V_{bias}$, and the second electrode 1404 is therefore given the electric potential needed for the redox recycling process.

One problem can result when a changeover is made between the two operating modes illustrated above, if neither of the two switches 917, 918 is closed.

The electrode voltage at the second electrode 1404 of the sensor 1401 can in this case in principle drift away from the desired voltage value.

In order to avoid such a problem, it is expedient to provide suitable timing for the changeover operation of the switches 917, 918 or to take additional switching measures, such as are provided in the more detailed exemplary embodiments described further below of the electric circuit 902.

Figure 10:
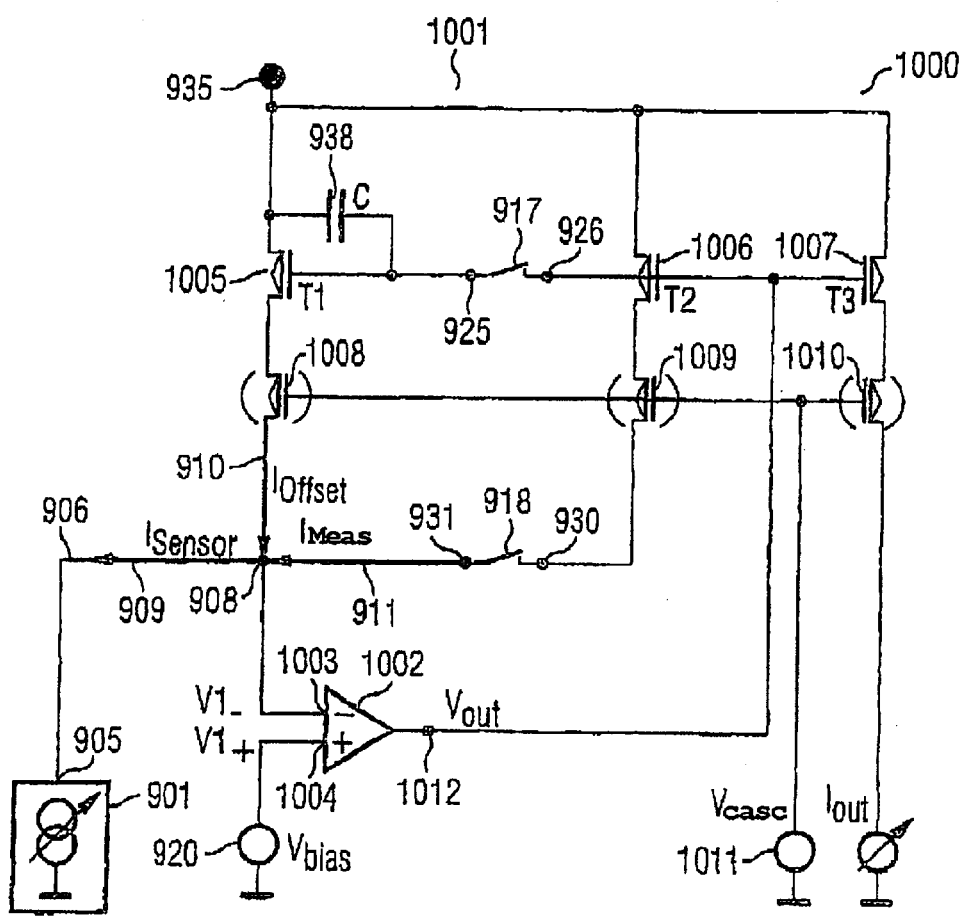
FIG. 10 shows a circuit diagram of an electronic circuit according to a first exemplary embodiment of the invention.

FIG. 10 shows an electronic circuit 1000 according to a first exemplary embodiment of the invention.

Identical structural elements with identical functionality of the electronic circuit 902 and the sensor 901 illustrated in principle in FIG. 9 are provided with identical reference symbols in the sensor arrangement 1000 according to the first exemplary embodiment.

The electronic circuit 1001 has, as the differential-voltage-controlled voltage source, an operational amplifier 1002, whose inverting input (negative input) 1003 is coupled to the first node 908 and whose non-inverting input (positive input) 1004 is connected to the bias voltage source 920.

The voltage-controlled current sources of the electronic circuit 902 are implemented, according to this exemplary embodiment and the further exemplary embodiments, by means of PMOS transistors, the first voltage-controlled current source 913 by means of a first transistor 1005, the second voltage-controlled current source 914 by means of a second transistor 1006 and the third voltage-controlled current source 915 by means of a third transistor 1007.

Alternatively, of course, other types of transistors can be used, for example CMOS transistors, BiCMOS transistors, bipolar transistors, etc.

Optionally, the additional further PMOS transistors 1008, 1009, 1010 illustrated in brackets and respectively connected in series with the respective transistors 1005, 1006, 1007, can be provided, the further transistors 1008, 1009, 1010 serving as a cascade and being connected to a cascade voltage $V_{casc}$ provided by a cascade voltage source 1011.

By means of the further transistors 1008, 1009, 1010, the current source characteristics of the transistors 1005, 1006, 1007 is improved. In other words, this means that the output resistance of the voltage-controlled current sources is increased.

In all the exemplary embodiments, as illustrated in FIG. 10, FIG. 11, FIG. 12, FIG. 13, in each case the drain terminal of the transistors 1005, 1006, 1007 is connected to one another and to the output 935 of the electronic circuit 1001, 1101, 1201, 1301.

The function of the electronic circuit 1001 and thus of the sensor arrangement 1000 according to the first exemplary embodiment will be described analytically below using some calculations.

The open-loop gain of the operational amplifier 1002 is designated A1.

As long as feedback ensures that the operational amplifier 1002 is not operated in its limiting range, the following are true:

$$V_{out} = A1(V_+ - V_-); \quad (3)$$

$$V_{out} = A1(V_{bias} - V_-); \quad (4)$$

$$V_- = V_{bias} - V_{out}/A1; \quad (5)$$

$$A1 \to \infty \Rightarrow V_- = V_{bias} \quad (6)$$

Irrespective of the operating mode of the control part 903, formed by the corresponding transistors and the control unit 919 and the operational amplifier 1002, given the existence of feedback between the operational amplifier output 1012, according to this exemplary embodiment via the first transistor 1005 or the second transistor 1006, and its inverting input 1003, the desired bias voltage value $V_{bias}$ is established at the second electrode 1404 of the sensor 1401, 901 as soon as the open-loop gain A1 is sufficiently high.

In the following calculations, a distinction is drawn between the two operating modes described above.

In the first operating mode of current offset compensation, that is to say during the first phase, the first switch 917 is closed and the second switch 918 is opened.

By using a simple transistor model for the saturation case, as described in [9] for example, the offset current $I_{offset}$ through the first transistor 1005 may be described by the following equation:

$$I_{offset} = k1([V_{dd} - V_{out}] - |V_{thp1}|)^2, \qquad (7)$$

where $V_{dd}$ designates the supply voltage, $V_{thp1}$ designates the turn-on voltage of the first transistor 1005, k1 designates a constant which is technology-specific and depends on the transistor geometry for the first transistor 1005.

If the above equation (7) is solved for the output voltage $V_{out}$, then a relationship is obtained between the voltage value $V_{memory}$ stored in the voltage value memory 916 and the current $I_{offset}$ dissipated in the offset channel 910, according to the following equation:

$$V_{memory} = V_{dd} - |V_{thp1}| - \sqrt{\frac{I_{offset}}{k1}}. \qquad (8)$$

According to the second operating mode, in which the first switch 917 is opened and the second switch 918 is closed, the relationships at the second transistor 1006 are described by the same transistor model presented above, and the result is:

$$I_{meas} = I_{sen} - I_{offset} = k2 \cdot (V_{dd} - V_{out} - |V_{thp2}|)^2 \qquad (9)$$

$$\Rightarrow V_{out} = V_{dd} - |V_{thp2}| - \sqrt{\frac{I_{sen} - I_{offset}}{k2}}$$

where $V_{thp2}$ designates the turn-on voltage of the second transistor 1006.

In addition, in the output part 904 of the electronic circuit 1001, the result is:

$$I_{out} = k3(V_{dd} - V_{out} - |V_{thp3}|)^2 \qquad (10)$$

$$= k3\left(V_{dd} - V_{dd} + |V_{thp2}| + \sqrt{\frac{(I_{sen} - I_{offset})}{k2}} - |V_{thp3}|\right)^2,$$

where $V_{thp3}$ designates the turn-on voltage of the third transistor 1007.

Assuming that the following is true:

$$V_{thp2} = V_{thp3}, \qquad (11)$$

the result is;

$$I_{out} = \frac{k3}{k2}(I_{sen} - I_{offset}). \qquad (12)$$

Since the sensor current $I_{sensor}$ according to FIG. 5 is given by the following equation:

$$I_{sensor} = I_{offset} + m \cdot t, \qquad (13)$$

the result is:

$$I_{out} = \frac{k3}{k2} \cdot m \cdot t. \qquad (14)$$

The output current $I_{out}$ contains the parameter m which is characteristic of the analysis of the redox recycling process and which contains the corresponding information content with regard to the DNA strand to be detected in the solution to be investigated.

The prefactor $$\frac{k3}{k2}$$

can be set appropriately by the circuit designer by means of the geometry of the second transistor 1006 and of the third transistor 1007, and therefore predefined.

The prefactor $$\frac{k3}{k2}$$

can therefore, for example, also be used as a gain factor.

Figure 11:
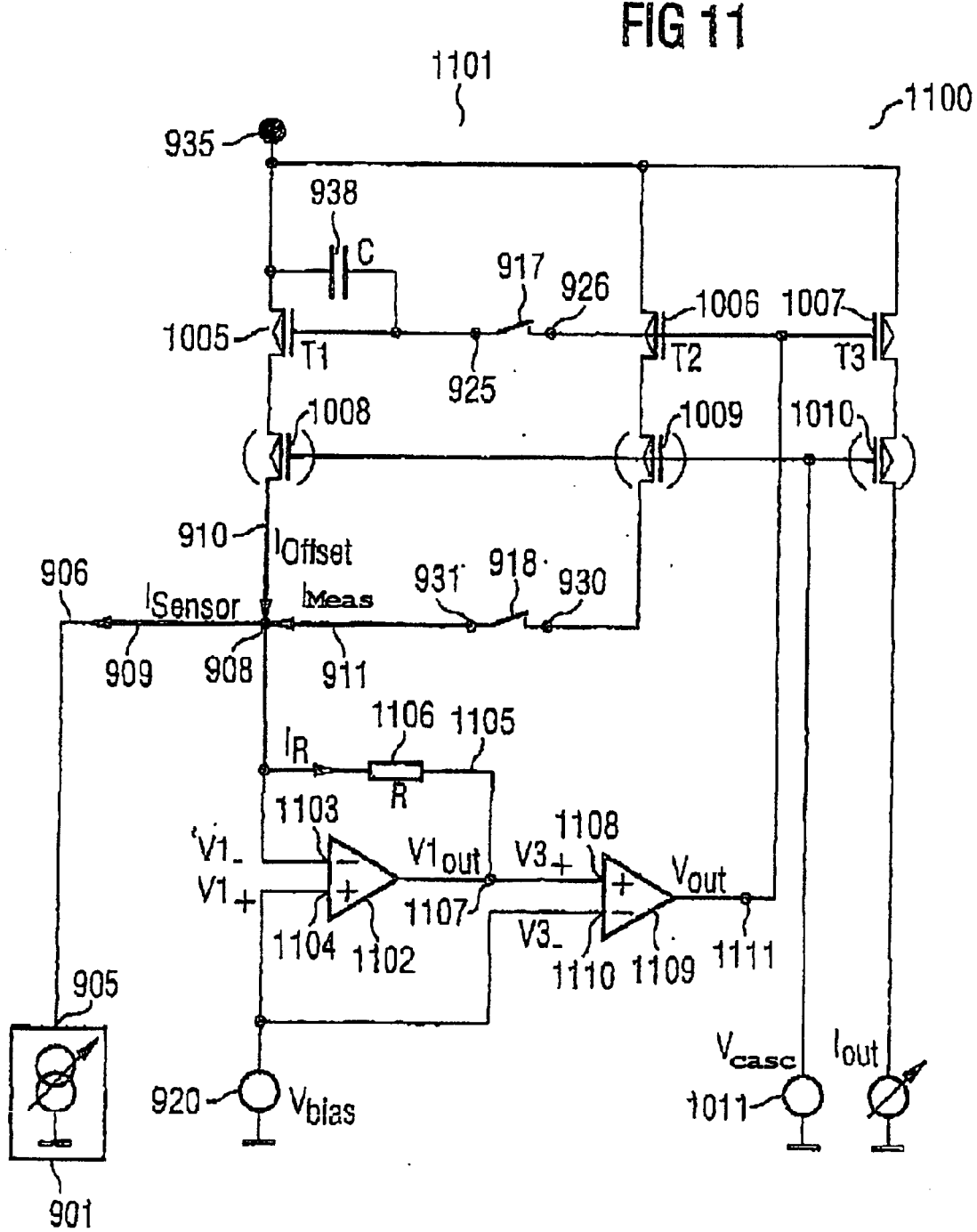
FIG. 11 shows a circuit diagram of an electronic circuit according to a second exemplary embodiment of the invention.

FIG. 11 shows a sensor arrangement 1100 according to a second exemplary embodiment of the invention.

Identical structural elements with identical functionality to the electronic circuit 902 and the sensor 901 illustrated in FIG. 9 and FIG. 10 are provided with identical reference symbols in the sensor arrangement 1100 according to the second exemplary embodiment.

The electronic circuit 1101 according to the second exemplary embodiment differs from the electronic circuit 1001 according to the first exemplary embodiment in particular in an additional operational amplifier, designated the second operational amplifier 1102 below, whose inverting input 1103 is coupled to the first node 908 and whose non-inverting input 1104 is coupled to the bias voltage source 920.

Furthermore, an electrical resistor 1106 is provided in the feedback branch 1105 of the second operational amplifier 1102.

The output 1107 of the second operational amplifier is coupled to the non-inverting input 1108 of the first operational amplifier 1109, and the non-inverting input 1104 of the second operational amplifier 1102 is coupled to the inverting input 1110 of the first operational amplifier 1109.

The output 1111 of the first operational amplifier 1109 is in turn coupled to the gate terminals of the second transistor 1006 and of the third transistor 1007.

By means of the additional second operational amplifier 1102 and the feedback resistor 1106, the second electrode 1404 of the sensor 1401, 905 is connected to the necessary desired bias voltage $V_{bias}$ irrespective of the position of the switches 917, 918, that is to say the following equations apply:

$$V_{1out} = A1(V_{1+} - V_{1-}); \qquad (15)$$

$$V_{1out} = A1(V_{bias} - V_{1-}); \qquad (16)$$

$$\Rightarrow V_{1-} = V_{bias} - V_{1out}/A1; \qquad (17)$$

$$A1 \to \infty \Rightarrow V_{-} = V_{bias}. \qquad (18)$$

Furthermore, the electronic circuit 1101 functions in exactly the same way as the electronic circuit 1001 according to the first exemplary embodiment, as soon as the current $I_R$ through the feedback resistor 1106 vanishes.

In order to calculate the voltage drop across the feedback resistor 1106, the voltage $V_{3+}$ on the non-inverting input 1110 of the first operational amplifier 1109 must be known.

As soon as the overall control loop has been coupled back to the first operational amplifier 1109 by closing one of the two switches 917, 918, and the output, that is to say the output voltage $V_{out}$, does not get into the saturation range of the operational amplifier 1102, 1109, the following equations apply:

$$V_{out} = A3(V_{3+} - V_{3-}); \tag{19}$$

$$V_{out} = A3(V_{3+} - V_{bias}); \tag{20}$$

$$\Rightarrow V_{3+} = V_{bias} + V_{out}/A3; \tag{21}$$

$$A3 \to \infty \Rightarrow V_{3+} = V_{bias} \tag{22}$$

The electric voltage drop across the feedback resistor 1106 is therefore equal to zero and, consequently, the current $I_R$ through the feedback resistor 1106 is also equal to zero, as required for the function of the electronic circuit 1101 according to the second exemplary embodiment, when one of the switches 917, 918 is closed.

According to the first exemplary embodiment and the second exemplary embodiment, the variable of interest of the current gradient rise m occurs linearly in the equation for determining the output current $I_{out}$ but non-linearly in the equation for determining the output voltage $V_{out}$.

According to the third exemplary embodiment described below and the fourth exemplary embodiment described below, the current gradient rise m is contained in linear form in both output variables $I_{out}$ and $V_{out}$.

In the calculation of the function of the electronic circuit 1201 illustrated in FIG. 12, once again the operating modes of the offset compensation and of the actual measurement phase are distinguished.

Figure 12:
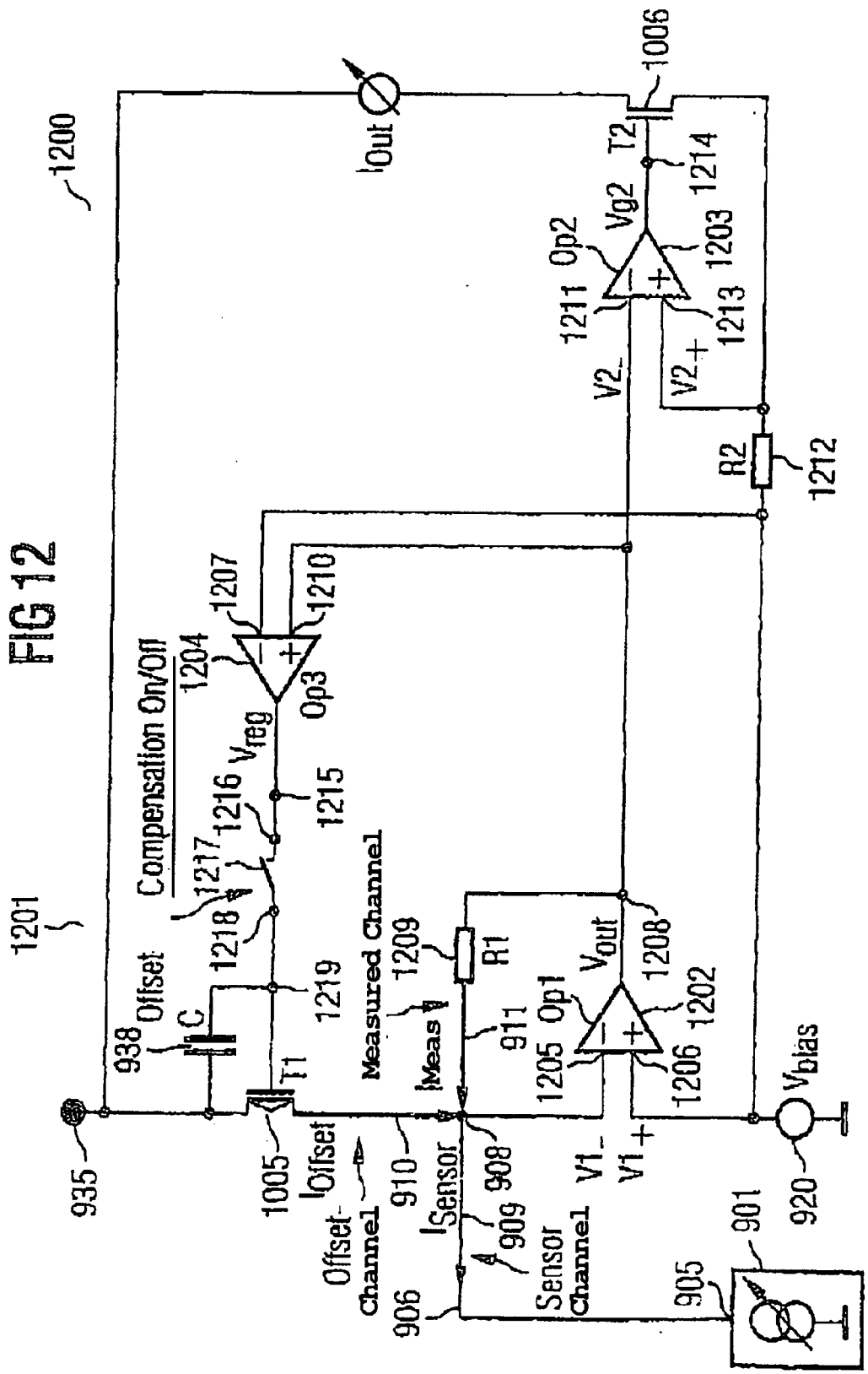
FIG. 12 shows a circuit diagram of an electronic circuit according to a third exemplary embodiment of the invention.

FIG. 12 shows a sensor arrangement 1200 according to a third exemplary embodiment of the invention.

Identical structural elements with identical functionality to the electronic circuit 902 and the sensor 901 illustrated in FIG. 9, FIG. 10 and FIG. 11 are provided with identical reference symbols in the sensor arrangement 1200 according to the third exemplary embodiment.

The electronic circuit 1201 according to the third exemplary embodiment has a third operational amplifier 1202, a fourth operational amplifier 1203 and a fifth operational amplifier 1204.

The inverting input 1205 of the third operational amplifier is coupled to the first node 908, and the non-inverting input 1206 is coupled to the bias voltage source 929 and to the inverting input 1207 of the fifth operational amplifier 1204.

Furthermore, the output 1208 of the third operational amplifier 1202 is fed back via the first electric resistor 1209 to the first node 908 and also coupled to the non-inverting input 1210 of the fifth operational amplifier 1204 and to the inverting input 1211 of the fourth operational amplifier 1203.

Furthermore, the non-inverting input 1206 of the third operational amplifier 1202 is coupled via a second electric resistor 1212 to the non-inverting input 1213 of the fourth operational amplifier 1203.

The output 1214 of the fourth operational amplifier 1203 is coupled to the gate terminal of the second transistor 1006, and the output 1215 of the fifth operational amplifier is coupled to a first terminal 1216 of a switch 1217, whose second terminal 1218 is coupled to the gate terminal 1219 of the first transistor 1005, and via a capacitor 938 to the drain terminal of the first transistor 1005 and the output 935 of the electronic circuit 1201.

Thus, the electronic circuit according to the third exemplary embodiment contains only switch 1217.

The output voltage $V_{out}$ can be calculated in accordance with the following equations:

$$V_{out} = A1(V_{1+} - V_{1-}); \tag{23}$$

$$V_{out} = A1(V_{bias} - V_{out} - I_{meas}R1); \tag{24}$$

$$\Rightarrow V_{out} = A1/(1+A1)(V_{bias} - I_{meas}R1). \tag{25}$$

For a control voltage $V_{reg}$, which, when the switch 1217 is closed, is identical to the voltage present on the gate terminal 1219 of the first transistor 1005, the result is:

$$V_{reg} = A3(V_{3+} - V_{3-}); \tag{26}$$

$$V_{reg} = A3(V_{out} - V_{bias}); \tag{27}$$

$$\Rightarrow V_{reg} = A3(A1/(1+A1)(V_{bias} - I_{meas}R1) - V_{bias}). \tag{28}$$

At the first node 908 of the electronic circuit 1201, the result according to Kirchhoff's law is therefore:

$$I_{sensor} = I_{offset} + I_{meas}. \tag{29}$$

The offset current $I_{offset}$ through the first transistor 1005 may be described by the simple transistor model already described above for the case of saturation in accordance with the following equation:

$$I_{offset} = k1([V_{dd} - V_{reg}] - |V_{thp}|)2. \tag{30}$$

The result is therefore three equations (28), (29), (30) for the three unknowns, that is to say for the measurement current $I_{meas}$, the offset current $I_{offset}$ and the control voltage $V_{reg}$.

Solving the equation system and forming a limiting value for the gain factors A1, A3 $\to \infty$ lead, inter alia, to the result that the offset current $I_{offset}$ is equal to the sensor current $I_{sensor}$, and the measurement current $I_{meas}$ is equal to zero.

Therefore, when the switch 1217 is closed, the effect of the electronic circuit 1201 is that all of the sensor current $I_{sensor}$ flows away into the offset channel 910.

If the switch 1217 is opened, then the control is interrupted.

The floating gate 1219 of the first transistor 1005 in this case stores the voltage value which corresponds to a specific offset current $I_{offset}$.

In this case, the capacitor C 938 functions as an optional supporting capacitor.

In the second operating mode, that is to say in the actual measurement phase, for the four unknowns, that is to say for the output current $I_{out}$, the output voltage $V_{out}$ and the variables $V_{g2}$ and $V_{2+}$, a corresponding number of equations (31), (32), (33), (34), that is to say four equations, may be set up, as described below:

$$V_{out} = A1/(1+A1)(V_{bias} - I_{meas}R1); \tag{31}$$

$$V_{g2} = A2(V_{2+} - V_{out}); \tag{32}$$

$$I_{out} = k2(V_{g2} - V_{2+} - V_{thn})2 \tag{33}$$

$$V_{2+} = V_{bias} + I_{out}R2. \tag{34}$$

The complete solution to the equation system and the formation of a limiting value for the gain factors A1, A2 $\to \infty$ lead to the following results:

$$I_{out} = -R1/R2 I_{meas} = -R1/R2 \; t \; m; \quad (35)$$

$$V_{out} = V_{bias} - I_{meas} R1 = V_{bias} - R1 \; t \; m. \quad (36)$$

In equations (35) and (36) for determining the two output variables, that is to say in the output current $I_{out}$ and the output voltage $V_{out}$ the parameter m now occurs only in linear form.

Via the ratio of the electric resistors R1, R2, a desired gain can be set for the current gradient rise m in the output current $I_{out}$.

Figure 13:
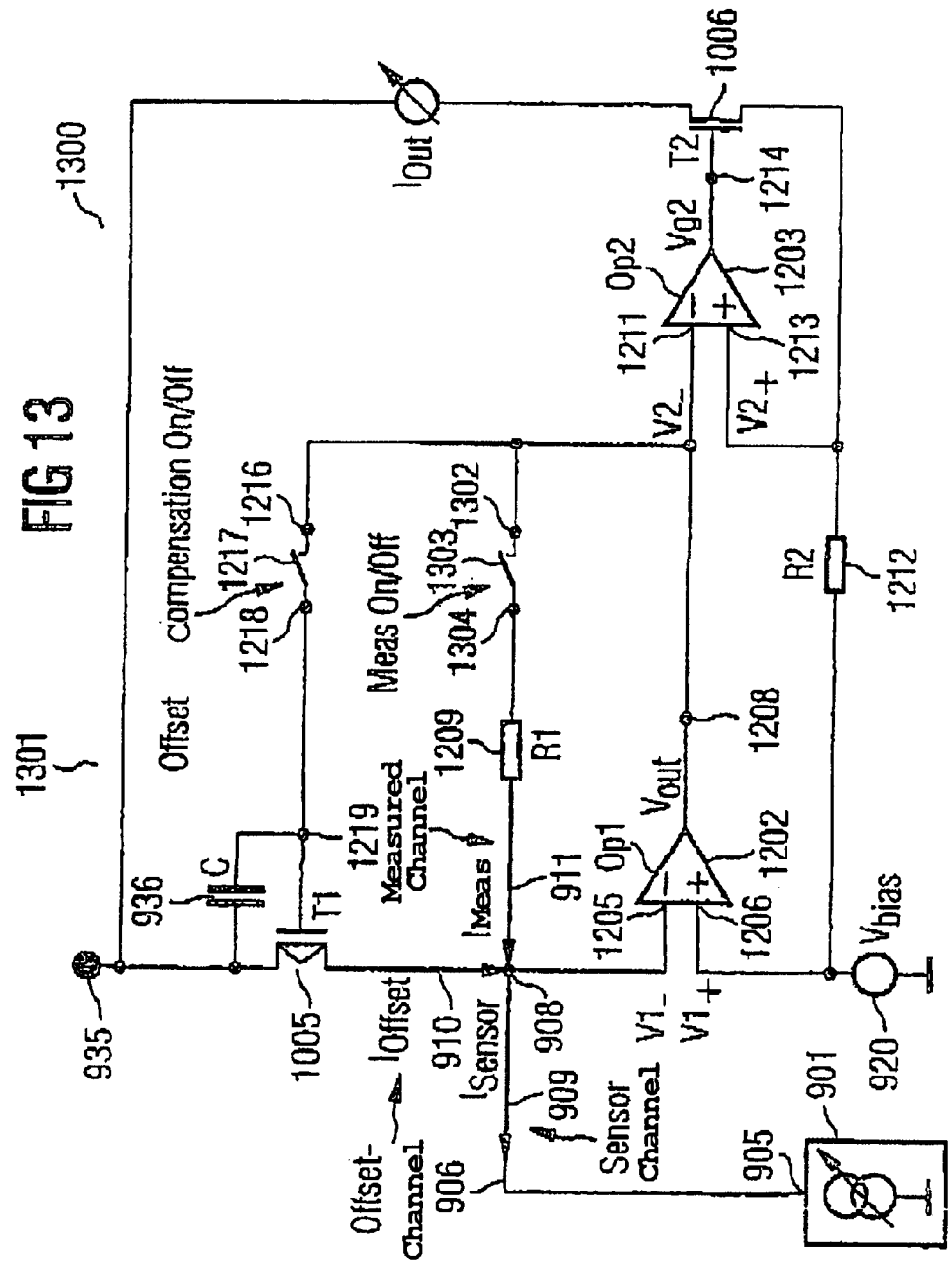
FIG. 13 shows a circuit diagram of an electronic circuit according to a fourth exemplary embodiment of the invention.

FIG. 13 shows a sensor arrangement 1300 according to a fourth exemplary embodiment of the invention.

Identical structural elements with identical functionality to the electronic circuit 902 and the sensor 901 illustrated in FIG. 9, FIG. 10, FIG. 11 and FIG. 12 are provided with identical reference symbols in the sensor arrangement 1200 according to the third exemplary embodiment.

The electronic circuit 1301 according to the fourth exemplary embodiment of the invention is a variant of the electronic circuit 1201 according to the third exemplary embodiment.

In the electronic circuit 1301 according to the fourth exemplary embodiment of the invention, the fifth operational amplifier 1204 is omitted, as compared with the electronic circuit 1201 according to the third exemplary embodiment of the invention.

The output 1208 of the third operational amplifier 1202 is coupled directly to the first terminal of the switch 1217 also provided in the electronic circuit 1201, and furthermore to a first terminal 1302 of a further switch 1303, whose second terminal 1304 is coupled to the electric resistor 1209 and via the latter in turn to the first node 908.

For the case in which neither of the switches 1217, 1303 is closed, according to this fourth exemplary embodiment, however, the potential on the second electrode 1404 can drift away from the predefined desired bias voltage value $V_{bias}$, so that in this case suitable timing for the changeover operation should be maintained.

The following publications are cited in this document;

[1] R. Hintsche et al., Microbiosensors Using Electrodes Made in Si-Technology, Frontiers in Biosensorics, Fundamental Aspects, edited by F. W. Scheller et al., Dirk Hauser Verlag. Basel, pp. 267–283, 1997
[2] M. Paeschke et al., Voltammetric Multichannel Measurements Using Silicon Fabricated Microelectrode Arrays, Electroanalysis, Vol. 7, No. 1, pp. 1–8, 1996
[3] R. Hintsche et al., Microbiosensors using electrodes made in Si-technology, Frontiers in Biosensorics, Fundamental Aspects, edited by F. W. Scheller et al., Birkhauser Verlag, Basel, Switzerland, 1997
[4] P. van Gerwen, Nanoscaled Interdigitated Electrode Arrays for Biochemical Sensors, IEEE, International Conference on Solid-State Sensors and Actuators, Chicago, pp. 907–910, 16.–19. Jun. 1997
[5] WO 93/22678
[6] DE 196 10 115 A1
[7] C. Krause et al., Capacitive Detection of Surfactant Adsorption on Hydrophobized Gold Electrodes, Langmuir, Vol. 12, No. 25, pp. 6059–6064, 1996
[8] V. Mirsky et al., Capacitive Monitoring of Protein Immobilization and Antigen-Antibody Reactions on Monomolecular Alkylthiol Films on Gold Electrodes, Biosensors & Bioelectronics, Vol. 12, No. 9–10, pp. 977–989, 1997
[9] K. Hoffmann, VLSI-Entwurf, [VLSI Design], Oldenbourg Verlag Munich, Vienna, ISBN 3-486-23870-1, pp. 308, 1996
[10] DE 196 09 621 C1
[11] U.S. Pat. No. 5,726,597
[12] U.S. Pat. No. 4,992,755
[13] U.S. Pat. No. 4,987,379
[14] U.S. Pat. No. 4,810,973
[15] U.S. Pat. No. 4,495,470
[16] U.S. Pat. No. 4,462,002
[17] U.S. Pat. No. 4,322,687
[18] U.S. Pat. No. 4,306,196
Elektor, 11/98, Applikator, MLX90308, Programmierbares Sensor-Interface, [programmable sensor interface], pp. 72–75, 1998
P. D. Wilson et al., Universal sensor interface chip (USIC): specification and applications outline, Sensor Review, Vol. 16, No. 1, pp. 18–21, ISSN 0260-2288, 1996

LIST OF REFERENCE SYMBOLS

100 Basic sketch
101 First graph
102 Current
103 Time
104 Sensor signal curve
105 Sensor channel
106 Offset channel
107 Measurement channel
108 Node
109 Current offset signal
110 Second graph
111 Current
112 Time
113 Time
114 Current
115 Measurement signal curve
116 Third graph
200 Sensor
201 Electrode
202 Electrode
203 Insulator
204 Electrode terminal
205 Electrode terminal
206 DNA probe molecule
207 Electrolyte
208 DNA stands
300 Interdigital electrode
400 Biosensor
401 First electrode
402 Second electrode
403 Insulator layer
404 Holding region of first electrode
405 DNA probe molecule
406 Electrolyte
407 DNA strand
408 Enzyme
409 Cleaveable molecule
410 Negatively charged first part molecule
411 Arrow
412 Further solution
413 Oxidized first part molecule
414 Reduced first part molecule
500 Graph
501 Electric current
502 Time
503 Current-time curve
504 Offset current
600 Time graph
601 Sensor current
602 First phase 603 Changeover time
604 Second phase
605 Start of redox recycling
606 Transient phase
607 Time
700 Second time graph
701 First current signal
702 Second current signal
703 Sensor current
704 Time
705 First dynamic range
706 Second dynamic range
800 Measurement signal graph
801 Threshold current
802 Measurement current
803 Time
804 Fixed dynamic range
900 Sensor arrangement
901 Sensor
902 Electronic circuit
903 Electronic input control part electronic circuit
904 Output part electronic circuit
905 Output of sensor
906 Electric line
907 Input electronic circuit
908 First node
909 Sensor channel
910 Offset channel
911 Measurement channel
912 Differential-voltage-controlled voltage source
913 First voltage-controlled current source
914 Second voltage-controlled current source
915 Third voltage-controlled current source
916 Voltage value memory
917 First switch
918 Second switch
919 Control unit
920 Bias voltage source
921 First terminal of first voltage-controlled current source
922 Second terminal of first voltage-controlled current source
923 First terminal of voltage value memory
924 Second terminal of voltage value memory
925 First terminal of first switch
926 Second terminal of first switch
927 Second node
928 First terminal of second voltage-controlled current source
929 Second terminal of second voltage-controlled current source
930 First terminal of second switch
931 Second terminal of second switch
932 Output of differential-voltage-controlled voltage source
933 First terminal of third voltage-controlled current source
934 Second terminal of third voltage-controlled current source
935 Output
936 First input of differential-voltage-controlled current source
937 Second input of differential-voltage-controlled current source
938 Capacitor
939 Capacitor
1000 Sensor arrangement
1001 Electronic circuit
1002 First operational amplifier
1003 Negative input of first operational amplifier
1004 Positive input of first operational amplifier
1005 First transistor
1006 Second transistor
1007 Third transistor
1008 Further transistor
1009 Further transistor
1010 Further transistor
1011 Cascade voltage source
1012 Output of first operational amplifier
1100 Sensor arrangement
1101 Electronic circuit
1102 Second operational amplifier
1103 Negative input of second operational amplifier
1104 Positive input of second operational amplifier
1105 Feedback line
1106 Feedback resistor
1107 Output of second operational amplifier
1108 Positive input of first operational amplifier
1109 First operational amplifier
1110 Negative input of first operational amplifier
1111 Output of first operational amplifier
1200 Sensor arrangement
1201 Electronic circuit
1202 Third operational amplifier
1203 Fourth operational amplifier
1204 Fifth operational amplifier
1205 Negative input of third operational amplifier
1206 Positive input of third operational amplifier
1207 Negative input of fifth operational amplifier
1208 Output of third operational amplifier
1209 Feedback resistor
1210 Positive input of fifth operational amplifier
1211 Negative input of fourth operational amplifier
1212 Second electric resistor
1213 Positive input of fourth operational amplifier
1214 Output of fourth operational amplifier
1215 Output of fifth operational amplifier
1216 First terminal switch
1217 Switch
1218 Second terminal switch
1219 Gate terminal of first transistor
1300 Sensor arrangement
1301 Electronic circuit
1302 First terminal of further switch
1303 Further switch
1304 Second terminal of further switch
1400 Sensor arrangement
1401 Sensor
1402 Electronic circuit
1403 First electrode
1404 Second electrode
1405 Substrate
1406 Adhesive layer
1407 DNA probe molecule
1408 Solution to be investigated
1409 DNA strand
1410 Enzyme
1411 Molecule to be cleaved
1412 Negatively charged part molecule
1413 Arrow
1414 Positively charged part molecule
1415 Negatively charged part molecule
1416 Sensor current
1417 Output current
1418 Output

What is claimed is:

1. An electronic circuit for processing a first sensor signal, which comprises a current offset signal and a time-dependent measurement signal, or a second sensor signal, which substantially comprises the current offset signal, with an input to which the first sensor signal or the second sensor signal can be applied, having a first signal path, coupled to the input, to read the current offset signal away, having a second signal path, coupled to the input, to lead the time-dependent measurement signal away, having a control unit which is set up such that control is carried out in such a way that, for the case in which the second sensor signal is applied to the input, the second sensor signal is carried substantially only by the first signal path, a voltage value storage element being contained in the first signal path, with which the second sensor signal can be stored when the second sensor signal is applied to the input, and in the case in which the first sensor signal is applied to the input, it being possible for the second sensor signal stored in the voltage value storage element to be supplied to the input.

2. The electronic circuit as claimed in claim 1 further comprising, having an output at which an output signal can be tapped off, having a switching element, with which the first signal path or the second signal path can be coupled to the output independently of each other or can be separated from the output.

3. The electronic circuit as claimed in claim 1, in which the voltage value storage element has at least one capacitor.

4. The electronic circuit as claimed in claim 1, in which in the first signal path has a first current source controlled by the control unit.

5. The electronic circuit as claimed in claim 4, in which the control unit is set up in such a way that, for the case in which the signal carried by the second signal path exceeds a predefined threshold value, the controlled first current source generates a current corresponding to the signal carried by the second signal path, which current can be supplied to the input.

6. The electronic circuit as claimed in claim 1, in which the control unit has a voltage source.

7. The electronic circuit as claimed in claim 6, in which the voltage source is configured as a voltage-controlled voltage source.

8. The electronic circuit as claimed in claim 7, in which the voltage source is configured as a differential-voltage-controlled voltage source.

9. The electronic circuit as claimed in one of claims 1 to 8, in which a controlled second current source is provided in the second signal path.

10. The electronic circuit as claimed in claim 1, comprising a controlled third current source which is connected between the output and the signal paths and which generates the output signal.

11. A sensor arrangement comprising an electronic circuit as claimed in claim 1.

12. The sensor arrangement as claimed in claim 11, in which the sensor arrangement with the electronic circuit is formed as an integrated circuit.

13. The sensor arrangement as claimed in claim 11 or 12, set up to detect macromolecular biopolymers.

14. A method for processing a sensor signal, which comprises a current offset signal and a time-dependent measurement signal the method comprising, applying, in a first phase, a first sensor signal to an input of an electronic circuit, the first sensor signal substantially comprising the current offset signal;

substantially leading the first sensor signal into a first signal path coupled to the input and is stored;

applying, in a second phase, a second sensor signal to the input, the second sensor signal comprising the current offset signal and a time-dependent measurement signal; and supplying, in the second phase, the stored first sensor signal to the input via the first signal path, so that the time-dependent measurement signal is substantially carried by a second signal path coupled to the input.

15. The method as claimed in claim 14, used to detect macromolecular biopolymers.

16. The method as claimed in claim 15, in which, in the second phase, the second sensor signal is determined by means of a sensor during a redox recycling process for detecting macromolecular biopolymers.

\* \* \* \* \*

UNITED STATES PATENT AND TRADEMARK OFFICE
CERTIFICATE OF CORRECTION

PATENT NO. : 6,922,081 B2
APPLICATION NO. : 10/399355
DATED : July 26, 2005
INVENTOR(S) : Frey et al.

It is certified that error appears in the above-identified patent and that said Letters Patent is hereby corrected as shown below:

On the Title page, in the item (30) labeled Foreign Application Priority Data, please delete priority application number "100 51 178" and insert --100 51 178.3--.

On page 2 of the Title page, under the heading OTHER PUBLICATIONS, column 1, 1st publication listing, 3rd line after "pp. 72-75" please add --1998--.

On page 2 of the Title page, under the heading OTHER PUBLICATIONS, column 2, 2nd publication listing, 4th line, page numbers, please delete "977-089" and insert --977-989--.

Column 25, line 5, pleas delete the word "read" and insert -- lead--.

Signed and Sealed this

Twenty-seventh Day of February, 2007

JON W. DUDAS
*Director of the United States Patent and Trademark Office*